US 6,597,946 B2

(12) United States Patent
Avrahami et al.

(10) Patent No.: US 6,597,946 B2
(45) Date of Patent: Jul. 22, 2003

(54) ELECTRONIC CARD FOR TRANSDERMAL DRUG DELIVERY AND ANALYTE EXTRACTION

(75) Inventors: Zohar Avrahami, Rehovot (IS); Yossi Gross, Moshav Mazor (IS); Ze'ev Sohn, Ginot Shomron (IS)

(73) Assignee: Transpharma Ltd., Yehud (IS)

(*) Notice: Subject to any disclaimer, the term of this patent is extended or adjusted under 35 U.S.C. 154(b) by 0 days.

(21) Appl. No.: 09/859,646

(22) Filed: May 17, 2001

(65) Prior Publication Data

US 2002/0038101 A1 Mar. 28, 2002

Related U.S. Application Data

(60) Continuation-in-part of application No. 09/635,892, filed on Aug. 10, 2000, which is a division of application No. 09/189,170, filed on Nov. 9, 1998, now Pat. No. 6,148,232.

(51) Int. Cl.⁷ .............................. A61N 1/30; A61B 5/04
(52) U.S. Cl. ........................................ 604/20; 600/372
(58) Field of Search .................... 604/19–20; 607/2, 607/3, 152; 600/391, 372

(56) References Cited

U.S. PATENT DOCUMENTS

| | | | |
|---|---|---|---|
| 3,964,482 A | 6/1976 | Gerstel et al. | |
| 4,775,361 A | 10/1988 | Jacques et al. | |
| 4,943,290 A | 7/1990 | Rexroth et al. | |
| 5,019,034 A | 5/1991 | Weaver et al. | |
| 5,135,478 A | 8/1992 | Sibalis | |
| 5,165,418 A | 11/1992 | Tankovich | |
| 5,196,709 A | 3/1993 | Berndt et al. | |
| 5,232,441 A | 8/1993 | Stephen et al. | |
| 5,246,867 A | 9/1993 | Lakowicz et al. | |
| 5,281,825 A | 1/1994 | Berndt et al. | |
| 5,328,452 A | 7/1994 | Sibalis | |

(List continued on next page.)

FOREIGN PATENT DOCUMENTS

| EP | 0547 482 | 6/1993 | ............ A61N/1/30 |
|---|---|---|---|
| WO | WO 93/10854 | 6/1993 | ............ A61N/1/30 |
| WO | WO 94/16765 | 8/1994 | ............ A61N/1/30 |
| WO | WO 94/27671 | 12/1994 | ............ A61N/1/30 |
| WO | WO 97/07734 | 3/1997 | ............ A61B/5/00 |
| WO | WO 00/69515 | 11/2000 | |
| WO | WO 00/74767 | 12/2000 | |
| WO | WO01/13989 A1 | 1/2001 | |

OTHER PUBLICATIONS

Henry et al., "Micromachined needles for the transdermal delivery of drug", IEEE 11ᵗʰ Annual International Workshop on Micro–Electro–Mechanical Systems, 1998, pp. 494–498.

Chizmadzhev, et al., "Electrical properties of skin at moderate voltages", Biophysics Journal, Feb. 1998, 74(2), pp. 843–856.

(List continued on next page.)

Primary Examiner—Sharon Kennedy
(74) Attorney, Agent, or Firm—Abelman, Frayne & Schwab

(57) ABSTRACT

Devices for facilitating transdermal passage of materials are provided. In a preferred embodiment, a device for delivering a substance to skin of a subject is provided. A substance storage unit is adapted to store the substance. An analysis unit is adapted to receive a portion of a body fluid of the subject, to analyze the portion, and to generate a signal responsive to the analysis of the portion. One or more electrodes are adapted to be placed at respective sites on the skin. A substance delivery unit is adapted to receive the signal, and, responsive thereto, to drive at least some of the one or more electrodes to apply to respective ones of the sites on the skin a current capable of ablating stratum corneum epidermidis of the skin, so as to facilitate delivery of the substance from the storage unit through the skin at the respective ones of the sites.

4 Claims, 9 Drawing Sheets

U.S. PATENT DOCUMENTS

| | | | |
|---|---|---|---|
| 5,380,272 A | 1/1995 | Gross | |
| 5,409,835 A | 4/1995 | Lakowicz et al. | |
| 5,421,817 A | 6/1995 | Liss et al. | |
| 5,423,803 A | 6/1995 | Tankovich et al. | |
| 5,439,440 A | 8/1995 | Hoffman | |
| 5,458,140 A | 10/1995 | Eppstein et al. | |
| 5,462,520 A | 10/1995 | Hofmann | 604/20 |
| 5,464,386 A | 11/1995 | Hofmann | 604/20 |
| 5,485,530 A | 1/1996 | Lakowicz et al. | |
| 5,500,437 A | 3/1996 | Saitoh et al. | |
| 5,571,149 A | 11/1996 | Liss et al. | |
| 5,582,168 A | 12/1996 | Samuels et al. | |
| 5,624,847 A | 4/1997 | Lakowicz et al. | |
| 5,628,310 A | 5/1997 | Rao et al. | |
| 5,631,169 A | 5/1997 | Lakowicz et al. | |
| 5,648,269 A | 7/1997 | Lakowicz et al. | |
| 5,660,991 A | 8/1997 | Lakowicz et al. | |
| 5,674,267 A | 10/1997 | Mir et al. | |
| 5,688,232 A | 11/1997 | Flower | |
| 5,688,233 A | 11/1997 | Hofmann et al. | 604/20 |
| 5,697,896 A | 12/1997 | McNichols et al. | |
| 5,720,772 A | 2/1998 | Eckhouse | |
| 5,722,397 A | 3/1998 | Eppstein | |
| 5,759,767 A | 6/1998 | Lakowicz et al. | |
| 5,792,049 A | 8/1998 | Eppstein et al. | |
| 5,860,421 A | 1/1999 | Eppstein et al. | |
| 5,871,469 A | 2/1999 | Eggers et al. | |
| 5,885,211 A | 3/1999 | Eppstein et al. | |
| 5,902,272 A | 5/1999 | Eggers et al. | |
| 5,911,223 A | 6/1999 | Weaver et al. | |
| 5,924,981 A | 7/1999 | Rothfritz et al. | |
| 5,938,657 A | 8/1999 | Assa et al. | |
| 5,964,726 A | 10/1999 | Korenstein et al. | |
| 5,983,130 A | 11/1999 | Phipps et al. | |
| 5,983,131 A | 11/1999 | Weaver et al. | |
| 6,002,482 A | 12/1999 | Rothfritz et al. | |
| 6,009,344 A | 12/1999 | Flower et al. | |
| 6,022,316 A | 2/2000 | Eppstein et al. | |
| 6,024,733 A | 2/2000 | Eggers et al. | |
| 6,030,399 A | 2/2000 | Ignotz et al. | |
| 6,041,253 A | 3/2000 | Kost et al. | |
| 6,045,502 A | 4/2000 | Eppstein et al. | |
| 6,050,988 A | 4/2000 | Zuck | |
| 6,055,451 A | 4/2000 | Bambot et al. | |
| 6,066,134 A | 5/2000 | Eggers et al. | |
| 6,076,012 A | 6/2000 | Swanson et al. | |
| 6,083,196 A | 7/2000 | Trautman et al. | |
| 6,088,606 A | 7/2000 | Ignotz et al. | |
| 6,090,106 A | 7/2000 | Goble et al. | |
| 6,104,952 A | 8/2000 | Tu et al. | |
| 6,117,109 A | 9/2000 | Eggers et al. | |
| 6,142,939 A | 11/2000 | Eppstein et al. | |
| 6,142,992 A | 11/2000 | Cheng et al. | |
| 6,148,232 A | 11/2000 | Avrahami | |
| 6,159,194 A | 12/2000 | Eggers et al. | |
| 6,173,202 B1 | 1/2001 | Eppstein et al. | |
| 6,183,434 B1 | 2/2001 | Eppstein | |
| 6,192,734 B1 | 2/2001 | Rothfritz et al. | |
| 6,210,402 B1 | 4/2001 | Olsen et al. | |
| 6,228,078 B1 | 5/2001 | Eggers et al. | |
| 6,235,020 B1 | 5/2001 | Cheng et al. | |
| 6,238,391 B1 | 5/2001 | Olsen et al. | |

OTHER PUBLICATIONS

"Instructions Manual for the Force 2 Electrosurgical Generator", Valleylab/TycoHealthcare Group LP, Boulder, Colorado, 1999.

U.S. Patent Application No.: 09/840,522, entitled: "Handheld apparatus and method for transdermal drug delivery and analyte extraction", filed Apr. 23, 2001.

U.S. Patent Application No.: 09/859,646, entitled: "Electronic card or transdermal drug delivery and analyte extraction", filed May 17, 2001.

U.S. Patent Appln 10/021,586.

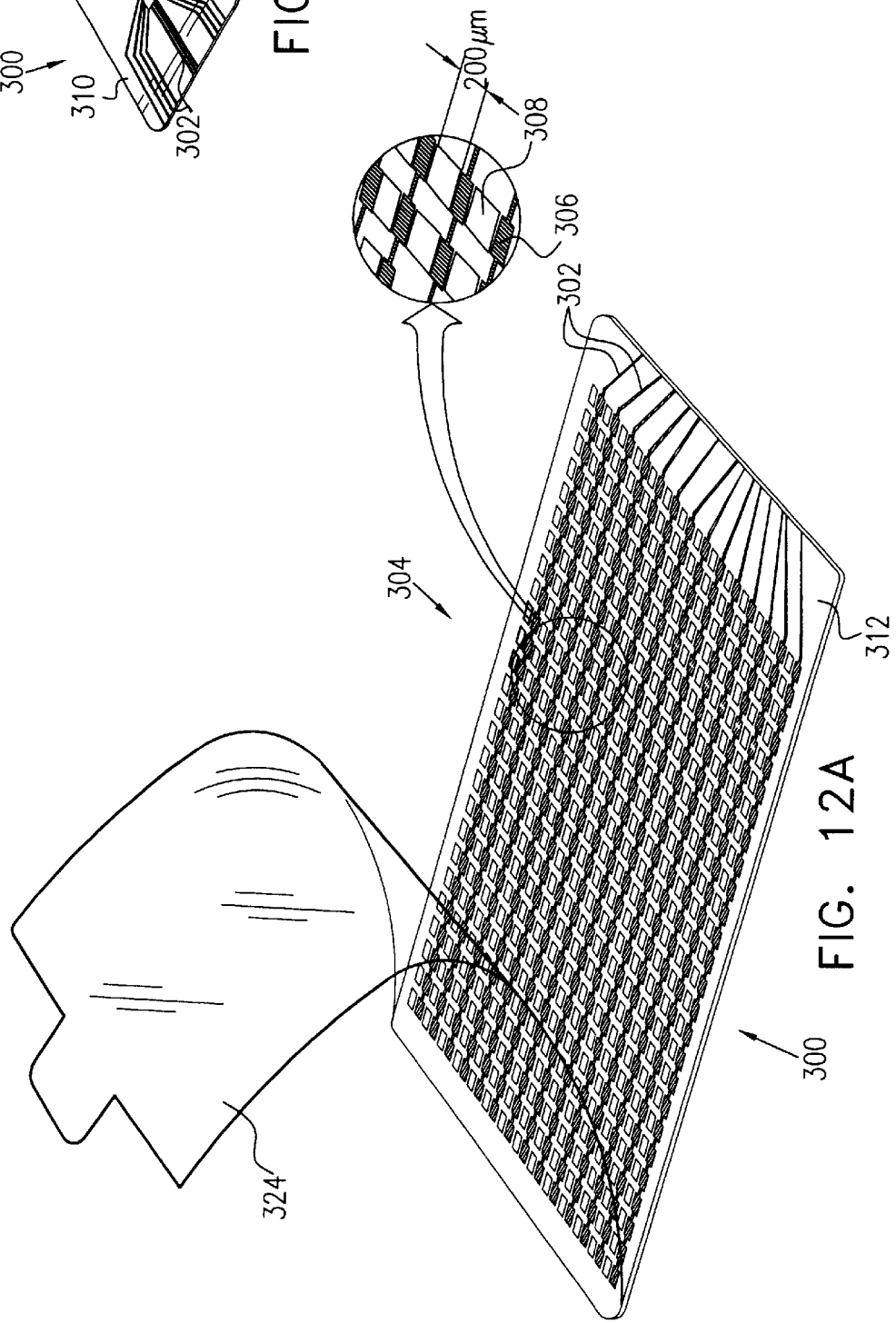
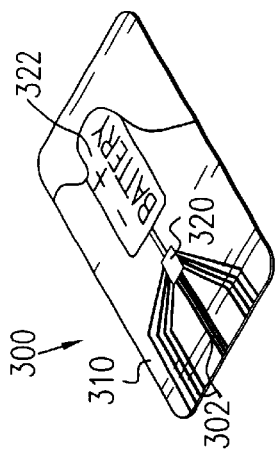
FIG. 12A
FIG. 12B

ELECTRONIC CARD FOR TRANSDERMAL DRUG DELIVERY AND ANALYTE EXTRACTION

CROSS-REFERENCE TO RELATED APPLICATIONS

This application is a continuation-in-part of U.S. patent application Ser. No. 09/635,892, entitled, "Transdermal drug delivery and analyte extraction," filed Aug. 10, 2000, which is a divisional based on U.S. patent application Ser. No. 09/198,170 (now U.S. Pat. No. 6,148,232), filed Nov. 9, 1998, entitled, "Transdermal drug delivery and analyte extraction." Both of these applications share common inventorship with the inventorship of the present patent application and are incorporated herein by reference.

FIELD OF THE INVENTION

The present invention relates generally to methods and devices for drug delivery and analyte extraction, and specifically to medical methods and devices for puncturing the outer layer of living skin and to methods and devices for transdermal drug delivery and analyte extraction.

BACKGROUND OF THE INVENTION

A number of different methods have been developed to perform transdermal drug delivery and/or analyte extraction, including passive diffusion of a drug or analyte between a skin patch and skin, as well as active processes such as iontophoresis, sonophoresis, electroporation, and chemically enhanced diffusion. These methods are primarily used for generating transdermal movement of small molecules, but generally do not enhance the motion of large molecules through the 10–50 micron thick outermost layer of the skin, the stratum corneum epidermidis.

In an article, "Micromachined needles for the transdermal delivery of drugs," IEEE 11th Annual International Workshop on Micro-Electro-Mechanical Systems (1998), pp. 494–498, which is incorporated herein by reference, Henry et al. discuss a method of mechanically puncturing the skin with microneedles in order to increase the permeability of skin to a test drug. In the article, microfabrication techniques are described to etch an array of needles in silicon, and experiments performed on cadaver skin with the needle array demonstrated an increase in permeability subsequent to puncture of the skin. The needles are created with a predetermined length, and penetrate to the same depth from the skin surface, regardless of the local thickness of the stratum corneum. It is known that if the needles are longer than the local thickness, then the underlying epidermal tissue may be injured, while if the needles are too short, channel formation through the stratum corneum may be incomplete.

U.S. Pat. Nos. 4,775,361, 5,165,418, and 5,423,803, and PCT Publication WO 97/07734, the disclosures of which are incorporated herein by reference, describe methods of using laser pulses to locally heat the stratum corneum to about 120° C., thereby causing local ablation, in order to cause a single hole to develop in the stratum corneum through which large molecules may pass. Whereas some selectivity of ablation depth can be attained by varying the wavelength of the laser pulse, no feedback mechanism is disclosed whereby the laser pulses are terminated upon generation of the necessary damage to the stratum corneum.

PCT Publication WO 97/07734 also discloses thermal ablation of the stratum corneum using an electrically resistive element in contact with the stratum corneum, such that a high current through the element causes a general heating of tissue in its vicinity, most particularly the stratum corneum. As above, no means are disclosed to terminate current flow upon sufficient disruption of the stratum corneum. Additionally, thermal characteristics of skin vary highly across different areas of an individual's skin, as well as among a group of subjects, making optimal thermal dosages, which produce the desired ablation without causing pain, very difficult to determine. Lastly, increasing transdermal molecular flow by increasing the permeability of the stratum corneum, whether using microneedles, laser energy, or resistive heating of tissue, is inherently a two step process: (a) position apparatus to generate holes, and (b) apply a patch to the skin, through which the molecules will flow.

Electroporation is also well known in the art as a method to increase pore size by application of an electric field. This process is described in an article by Chizmadzhev et al., entitled "Electrical properties of skin at moderate voltages," Biophysics Journal, February, 1998, 74(2), pp. 843–856, which is incorporated herein by reference. Electroporation is disclosed as a means for transiently decreasing the electrical resistance of the stratum corneum and increasing the transdermal flux of small molecules by applying an electric field to increase the size of existing pores. Electroporation generally does not produce pores of sufficient diameter to pass large molecules therethrough. Additionally, optimal voltage profiles are difficult to determine because of naturally occurring variations as described hereinabove, as well as the lack of an accurate feedback mechanism to indicate achievement of the desired pore enlargement. If excessive voltage is applied, an irreversible breakdown occurs, resulting in damage to the skin and possible sensations of pain.

U.S. Pat. No. 5,019,034 to Weaver et al., whose disclosure is incorporated herein by reference, describes apparatus for applying high voltage, short duration electrical pulses on the skin to produce electroporation, and states that ". . . reversible electrical breakdown . . . along with an enhanced tissue permeability, is the characteristic effect of electroporation."

SUMMARY OF THE INVENTION

It is an object of some aspects of the present invention to provide improved apparatus and methods for transdermal delivery of an active substance.

It is a further object of some aspects of the present invention to provide improved apparatus and methods for transdermal analyte extraction.

It is yet a further object of some aspects of the present invention to provide improved apparatus and methods for creating narrow channels through the stratum corneum of living skin by puncturing.

It is still a further object of some aspects of the present invention to provide improved apparatus and methods for reducing sensation and minimizing damage to skin underlying the stratum corneum during channel creation.

It is an additional object of some aspects of the present invention to provide improved apparatus and methods for controlling the timing of channel creation.

It is yet an additional object of some aspects of the present invention to provide improved apparatus and methods for regulating channel creation responsive to properties of the skin.

It is another object of some aspects of the present invention to provide improved apparatus and methods for puncturing the skin and/or transdermally delivering an active substance and/or transdermally extracting an analyte, using a miniature, self-contained device.

It is yet another object of some aspects of the present invention to provide improved apparatus and methods for transdermally delivering an active substance using a standard medical skin patch.

In preferred embodiments of the present invention, a device for enhancing transdermal movement of a substance comprises: (a) a skin patch, with at least two electrodes in contact with the skin of a subject; and (b) a control unit, coupled to the patch, which causes a current to pass between the electrodes through the stratum corneum epidermidis, in order to generate at least one micro-channel in the stratum corneum to enable or augment transdermal movement of the substance. Preferably, the control unit comprises switching circuitry to control the magnitude and/or duration of the electric field at the electrode.

The term "micro-channel" as used in the context of the present patent application and in the claims refers to a pathway generally extending from the surface of the skin through all or a significant part of the stratum corneum, through which pathway molecules can diffuse. Preferably, micro-channels allow the diffusion therethrough of large molecules at a greater rate than the same molecules would diffuse through pores generated by electroporation. It is believed that such micro-channels are formed due to local power dissipation leading to ablation of the stratum corneum when an electric field of sufficient magnitude is applied to a small area of the skin, in contact with the electrodes, for a certain period of time. Unlike methods of electrically-promoted drug delivery known in the art, such as iontophoresis and electroporation, the present invention enables relatively large channels to be formed, through which even large molecules of the active substance can pass rapidly, without the necessity of ionizing or polarizing the molecules.

The current flow between the electrodes can be described as having two components: (a) a perpendicular component, which is generally perpendicular to the skin surface (and, if the associated electric field is sufficiently large, may cause current to go through the stratum corneum into the underlying epidermal tissue and dermis); and (b) a lateral component, generally parallel to the skin surface, which remains generally within the stratum corneum. Substantially all of the current generated at one electrode ultimately emerges from the skin and is taken up by an adjacent electrode.

In preferred embodiments of the present invention, methods and/or apparatus are employed to increase the relative value of the lateral component with respect to the perpendicular component. In general, the stratum corneum epidermidis (the superficial layer of the epidermis) demonstrates a significantly higher resistance to the passage of molecules therethrough than does the underlying epidermal tissue. It is therefore an object of these preferred embodiments of the present invention to form micro-channels in the stratum corneum by ablating the stratum corneum in order to increase conductance of the substance therethrough, and to generally not directly affect or damage epidermal tissue underlying the stratum corneum or in the innervated dermis. Additionally, limiting current flow substantially to the non-innervated stratum corneum is expected to decrease or eliminate the subject's sensations, discomfort, or pain responsive to use of the present invention, particularly as compared with other procedures known in the art.

A voltage applied between two electrodes on the skin generates an electric field that is to a large extent confined to the volume in a vicinity of the electrodes. Thus, electrodes which are widely spaced produce a field—and current flow responsive thereto—which extends relatively deep into the skin. Conversely, electrodes which are closely spaced do not generate significant current flow at deeper layers. Therefore, in some preferred embodiments of the present invention, the electrodes of the device are separated by distances smaller than about 100 microns (but for some applications by distances of up to approximately 500 microns), in order to generate a current flow which is largely confined to a thin layer, comprising most or all of the stratum corneum. This effectively results in a desired larger value of the ratio of the lateral component to the perpendicular component, as described hereinabove.

In some of these preferred embodiments of the present invention, a high-frequency AC current with an optional DC current added thereto is applied between the closely-spaced electrodes in order to generate lateral capacitive currents in the stratum corneum and to cause breakdown and micro-channel formation in the stratum corneum.

In some preferred embodiments of the present invention, the patch comprises an array of electrodes, preferably closely-spaced electrodes, which act together to produce a high micro-channel density in an area of the skin under the patch. Preferably, the control unit and/or associated circuitry sequentially or simultaneously evaluates the current flow through each electrode, or a subset of the electrodes, in order to determine when one or more micro-channels have formed responsive to the applied field. Responsive thereto, the control unit discontinues application of the field. Since the formation of a micro-channel is typically marked by a local drop in electrical resistance of the skin, the control unit may, for example, reduce the voltage or current applied at any electrode wherein the current has exceeded a threshold. By reducing current flow upon or shortly after micro-channel formation, the likelihood of skin burns or pain sensations is minimized.

In some preferred embodiments of the present invention, a relatively high voltage is applied to the electrodes initially, so as to induce formation of micro-channels through the skin. A property of the current flow is detected, and the current is reduced or terminated when the property reaches a predetermined threshold. Preferably, the detected property of the current flow is secondary to changes in a conduction property of the skin, responsive to formation of one or more micro-channels through the stratum corneum.

Alternatively or additionally, a time-varying voltage V(t), characterized, for example, by the formula $V(t)=V_O+kt^n$, is applied between a first electrode and a second electrode in the skin patch until a shut-off signal is generated. (Constants k and n are nonnegative.) Other forms of V(t) may include a sinusoid, an exponential term, or a series of pulses. A current I(t), flowing responsive to the applied field, is measured by the control unit, as described hereinabove. Calculations of the values of $\int I(t)dt$, $dI/dt$ and/or $d^2I/dt^2$ are frequently performed. Comparisons of I and/or $\int I(t)dt$ and/or $dI/dt$ and/or $d^2I/dt^2$ with respective threshold values are used as indicators of micro-channel formation and/or to determine when to generate the shut-off signal for the electrodes.

Further alternatively or additionally, in embodiments in which V(t) is sinusoidal, the control unit preferably calculates changes in a phase shift between V(t) and I(t) during application of the electric field, and controls the field responsive to these changes. It is believed that cells in the stratum corneum demonstrate capacitance, which causes the phase shift, and that ablation of the stratum corneum decreases the capacitance and is evidenced by a decrease in the phase shift.

Still further alternatively or additionally, the total charge which is passed through the skin is limited by a capacitor, inductor, or other energy-storage device. An appropriate choice of values for these components sets an absolute maximum quantity of charge which can pass through the skin, and thus limits any damage that can be caused thereby.

In some preferred embodiments of the present invention, one or more of the electrodes comprise or are coupled to an electrically conductive dissolving element, where the dissolving rate is generally proportional to the current passing through the electrode. When a sufficient quantity of charge has passed through the dissolving element, the electrode ceases to conduct electricity. Thus, a maximum total charge, $Q_{total}$, is associated with an electrode, such that current flows through the element for only as long as $q(t)=\int I(t)dt<Q_{total}$. This serves as a safety feature, reducing the possibility of skin burns secondary to applied electric fields. Alternatively or additionally, the dissolving element is constructed so that it becomes non-conductive after a quantity of charge has passed therethrough which is sufficient to ablate the stratum corneum.

In some further preferred embodiments of the present invention, the electrodes are "printed" directly on the skin, preferably by stamping or by employing a transfer patch of a conductive substance (such as, for example, a conductive ink containing silver grains). In applications of such embodiments of the present invention for transdermal drug delivery, the conductive substance preferably comprises a matrix holding the drug to be administered to a subject.

Preferably, the printed electrodes demonstrate a substantially complete loss of conductance therethrough upon ablation of the stratum corneum responsive to the applied electric field. Further preferably, each printed electrode comprises a material which is conductive only when current flowing therethrough remains below a threshold value. If the current exceeds the threshold, then thermal fusion of the material causes it to become largely nonconductive, i.e. the material acts as a fuse. Still further preferably, current continues to flow through the other electrodes until they reach the threshold current, at a time which is generally associated with the time required for ablation of the stratum corneum, as described hereinabove. In some of these embodiments, the control unit may be made substantially simpler than as described regarding other embodiments, and generally does not need other circuitry in order to determine whether to generate a shut-off signal.

In still further preferred embodiments of the present invention, two electrodes on the patch form a concentric electrode pair, in which an inner electrode generates a current which passes through the stratum corneum to an outer electrode surrounding the inner electrode. The distance between the inner and outer electrodes is preferably between about 50 and about 200 microns, or between 200 microns and about several millimeters, in order to maintain the ratio of the lateral to the perpendicular component of the current at a high value, as described hereinabove.

In some preferred embodiments of the present invention, a conductance-enhancing substance, preferably comprising a conductive cream or ink, is applied to the skin in order to increase the ratio of the lateral to the perpendicular component of current flow. Alternatively or additionally, the conductance-enhancing substance comprises a composition with a high diffusion coefficient, which diffuses into the lipid layers of the stratum corneum and further augments the selective power dissipation therein, in order to ablate the stratum corneum with substantially little damage to the underlying tissue. In some applications, the substance has an electrical charge associated therewith, such that when a small lateral field is applied, lateral diffusion of the substance within the stratum corneum is enhanced (i.e., iontophoresis of the substance).

In some of these preferred embodiments which utilize a conductance-enhancing substance, the substance further comprises an active substance, for example, a pharmaceutical product, dissolved or mixed therein. Since breakdown of the stratum corneum is often associated with removal of the enhanced conductivity path afforded by the conductance-enhancing substance, it is preferable in many of these embodiments to use a substantially constant voltage source to generate current at the electrodes. Removal of the enhanced conductivity path will result in a desired reduced power dissipation in the stratum corneum ($P=V^2/R$), since the voltage remains constant while resistance increases.

In other preferred embodiments of the present invention, ablation of the stratum corneum is accomplished using a current-limited source to power the electrodes. It is believed that the stratum corneum generally displays high electrical resistance, while epidermal tissue underlying the stratum corneum has significantly lower electrical resistance. Ablation of the stratum corneum (i.e., removal of the high-resistance tissue) is therefore associated with a net decrease of electrical resistance between the electrodes, and the power dissipated in the epidermis following electrical breakdown will decrease, typically proportional to the change in resistance ($P=I^2R$).

Monitoring changes in voltage, current, and/or phase for each electrode in the control unit may require, in certain implementations, a significant amount of circuitry. Therefore, in some preferred embodiments of the present invention, the control unit comprises one or more clusters of electrodes, in which monitoring and control are performed for each cluster rather than for the individual electrodes therein, The cluster is preferably over a relatively small area of skin, for example, from about 1 $mm^2$ to about 100 $mm^2$, in which properties of the skin are assumed to be substantially constant.

In some preferred embodiments of the present invention, the device is a stand-alone device, which enables transdermal delivery of an active substance or enhances transdermal motion of an analyte. Alternatively, the device creates micro-channels as described hereinabove and is then removed from the skin, in order to enhance the transdermal delivery of a substance into or out of a commercially-available skin patch subsequently placed on the skin. In other preferred embodiments of the present invention, the device is an add-on to commercially available transdermal drug delivery/analyte extraction devices, and serves primarily to create the micro-channels in the stratum corneum, and optionally to act as a vehicle through which the substance may pass.

In further preferred embodiments of the present invention, the device is integrated into a package approximately the size and shape of a credit card, upon the underside of which is disposed an electrode array and a drug delivery unit. The electrode array preferably comprises a plurality of linear electrode elements, each electrode element comprising a plurality of equally-spaced individual electrodes, connected in series. In a preferred embodiment, electrodes in adjacent linear electrode elements in the electrode array are separated by about 200 microns to about several millimeters. Preferably, spaces between the electrodes in the electrode array form the drug delivery unit, and are used to store a drug which is actively or passively delivered to the skin following the ablation thereof. Further preferably, a cover on the underside of the card is removed prior to use, in order to expose the electrodes, the drug, and an adhesive which secures the card to the subject's skin.

In some preferred embodiments of the present invention, the device enables transdermal delivery of an active substance in conjunction with analyte extraction and analysis of the analyte. In a preferred embodiment, the device delivers an active substance through the skin of the subject, and subsequently extracts an analyte through the skin to facilitate the determination of the level of a relevant biological substance. In another preferred embodiment, the device first extracts an analyte through the subject's skin, then performs an analysis of the analyte, and subsequently determines an appropriate dose of an active substance to deliver to the subject. Alternatively or additionally, the extraction and analysis of the analyte are performed to determine which of a plurality of active substances to deliver to the subject.

In accordance with a further preferred embodiment of the present invention, the device comprises a sensor, which detects other physiological parameters of the subject, such as, but not limited to, blood pressure, temperature, heart rate, and respiration rate. Preferably, these parameters are analyzed to assist in the determination of the type or quantity of active substance to be delivered to the subject. Further preferably, the analysis of the physiological parameters is used to determine the timing of the delivery of the active substance.

In a preferred embodiment of the present invention, the device comprises a body fluid analysis unit, into which the subject deposits, for example, a sample of blood, urine, or saliva. Preferably, the body fluid analysis unit is included on the card with the electrodes and drug delivery unit, allowing results of analysis of the body fluid to be used in determining parameters of the treatment performed by the device. For example, the current level supplied to the electrodes, the type and amount of drug to be delivered to the subject, or the scheduling of drug delivery may be determined responsive to results of the body fluid analysis.

For some applications, the device comprises a pressure generation unit that is used to propel the active substance onto ablated regions of skin. Typically, an electric current passed through a liquid stored in the device generates a gas which creates a desired amount of pressure to facilitate the transfer of active substance into the skin.

Alternatively or additionally, the device comprises a transport facilitation unit comprising an ultrasonic transducer which increases the transport of the active substance into the skin, e.g., by imparting high energy to molecules of the active substance and/or by enhancing conductance of the skin to the substance. Further alternatively or additionally, iontophoresis or other methods known in the art are employed to improve the transfer of the active substance into the skin of the subject, the transfer being initially facilitated by ablation of the stratum corneum.

In a preferred embodiment of the present invention, the device comprises a timing unit, which allows the active substance to be delivered to the skin on a specified schedule, e.g., three times a day. Alternatively or additionally, ablation of the skin is initiated in accordance with a schedule set by the timing unit and another factor, such as eating or sleeping. Further alternatively or additionally, the timing unit initiates analyte extraction and analysis on a specified schedule, such that the active substance is delivered to the skin as necessary. For example, blood sugar could be tested every hour, and insulin delivered to the subject responsive to the blood sugar level. For some applications, particularly to facilitate a diagnosis, the timing unit is configured to initiate analyte extraction and analysis at a specified time after the active substance has been delivered to the skin. This allows the active substance the prescribed time to enter the subject and produce a desired effect before testing occurs.

Preferably, the device comprises an output unit to communicate relevant information to the subject. For example, the subject may be informed regarding the status of the device, the outcome of analyte analysis, and the amount of active substance delivered to the subject. Preferably, the output unit comprises a speaker, to give an audible output, and/or a display, such as an LCD, to present visual information to the subject.

In a preferred embodiment of the present invention, the device comprises an infrared or other wireless or wired data port for transferring data to or receiving instructions from another computer. For example, transmitted data may be designated for storage in a local computer or for analysis by a computer or physician at a remote healthcare facility. In a preferred application, the data port transmits the amount and timing of drug delivered to the subject, and/or results of analyte or body fluid analysis. Typically, the data port is configured to transmit the data to a local computational device, such as a computer, a personal digital assistant (PDA) or a cellular telephone, from which the data can subsequently be accessed by a health care professional at a remote site. Preferably, the health care professional is enabled to respond to the received information by sending instructions back to the device, such that the device changes one or more operational parameters thereof responsive to the instructions.

There is therefore provided, in accordance with a preferred embodiment of the present invention, a device for delivering a substance to skin of a subject, including:

a substance storage unit, which is adapted to store the substance;

a sensor, which is adapted to generate a sensor signal responsive to a physiological parameter of the subject;

one or more electrodes, which are adapted to be placed at respective sites on the skin; and a substance delivery unit, which is adapted to receive the signal, and, responsive thereto, to drive at least some of the one or more electrodes to apply to respective ones of the sites on the skin a current capable of ablating stratum corneum epidermidis of the skin, so as to facilitate delivery of the substance from the storage unit through the skin at the respective ones of the sites.

Preferably, the sensor includes an analysis unit, which is adapted to receive a portion of a body fluid of the subject, to analyze the portion, and to generate the sensor signal responsive to the analysis of the portion. Alternatively or additionally, the analysis unit is adapted to drive at least one of the one or more electrodes to apply a substantially DC current to the skin so as to enhance by means of iontophoresis extraction through the skin of the portion of the body fluid. Still further alternatively or additionally, the analysis unit is adapted to analyze the portion of the body fluid to determine a level of sugar in blood of the subject, and to generate the signal responsive thereto. For example, the substance storage unit may be adapted to store insulin.

In a preferred embodiment, the substance delivery unit is adapted:

to designate at a first time a first number of the one or more electrodes to drive to apply the current, responsive to a desired rate of delivery of the substance during a first time period, and to designate at a second time a second number of the one or more electrodes to drive to apply the current, responsive to a desired rate of delivery of the substance during a second time period, the second number being different from the first number.

Alternatively or additionally, the substance delivery unit is adapted to:

drive a first subset of the one or more electrodes to apply during a first time period, a current capable of ablating stratum corneum in a vicinity of the first subset of the one or more electrodes, and drive a second subset of the one or more electrodes to apply, during a second time period, a current capable of ablating stratum corneum in a vicinity of the second subset, wherein the second subset includes at least one electrode which is not in the first subset.

Still further alternatively or additionally, the substance delivery unit is adapted to drive a subset of the one or more electrodes to apply:

during a first time period, a current capable of ablating stratum corneum in a vicinity of the subset of the one or more electrodes, and during a second time period, a current capable of ablating stratum corneum in the vicinity.

In a preferred embodiment, the sensor is adapted to measure a property of skin in the vicinity.

For some applications, at least one of the one or more electrodes is adapted to apply to the skin a substantially DC current capable of enhancing by means of iontophoresis the passage of a material through the skin. For example, the substance delivery unit may be adapted to drive the at least one of the one or more electrodes to apply the substantially DC current to the skin so as to enhance by means of iontophoresis the delivery of the substance through the skin.

Preferably, the device includes a transport facilitation unit, adapted to facilitate transport of a material through the skin.

In a preferred embodiment, the device includes a communications unit, which is adapted to receive the signal and, responsive thereto, to transmit information to a computer external to the device. Alternatively or additionally, the device includes a communications unit, which is adapted to receive an instruction from a remote computer, and wherein the substance delivery unit is adapted to modify, responsive to the instruction, a parameter of the current.

In a preferred embodiment, the sensor includes an analysis unit which is adapted to drive a subset of the one or more electrodes to apply a current to the skin, so as to facilitate extraction therefrom of an analyte in a body fluid of the subject. For example, the analysis unit may be adapted to drive the subset of the one or more electrodes to apply a current to the skin capable of ablating stratum corneum epidermidis of the skin.

For some applications, the sensor includes an analysis unit which is adapted to analyze at least one of; blood of the subject, urine of the subject, and saliva of the subject, and to generate the signal responsive thereto.

There is further provided, in accordance with a preferred embodiment of the present invention, a device for delivering a substance to skin of a subject, including:

a housing;

a set of electrodes, fixed to the housing, which set of electrodes is adapted to be placed at respective sites on the skin;

an analysis unit, fixed to the housing, which analysis unit is adapted to drive a first subset of the set of electrodes to apply a current to the skin so as to facilitate extraction therefrom of an analyte, to analyze the analyte, and to generate a signal responsive to the analysis of the analyte;

a substance storage unit, fixed to the housing, which storage unit is adapted to store the substance; and a substance delivery unit, fixed to the housing, which delivery unit is adapted to receive the signal, and, responsive thereto, to drive a second subset of the set of electrodes to apply current to the skin so as to facilitate delivery of the substance from the storage unit through the skin.

In a preferred embodiment, the device includes a transport facilitation unit, adapted to facilitate transport of a material through the skin.

In a preferred embodiment, the analysis unit is adapted to drive the first subset of the set of electrodes to apply a substantially DC current to the skin, to enhance by means of iontophoresis the extraction of the analyte through the skin. Alternatively or additionally, the substance delivery unit is adapted to drive the second subset of the set of electrodes to apply a substantially DC current to the skin to enhance by means of iontophoresis the delivery of the substance through the skin.

For some applications, the first subset of electrodes includes at least one electrode in the second subset of electrodes. For other applications, the first subset of electrodes consists exclusively of electrodes which are not in the second subset of electrodes.

There is yet further provided, in accordance with a preferred embodiment of the present invention, a device for analyzing an analyte extracted through skin of a subject, including:

one or more electrodes, which are adapted to be placed at respective sites on the skin;

a control unit, which is adapted to drive the one or more electrodes to apply a current to the respective sites on the skin capable of ablating stratum corneum epidermidis of the skin, so as to facilitate extraction of the analyte through the skin;

an analysis unit, which is adapted to analyze the analyte and to generate a signal responsive to the analysis of the analyte; and a communications unit, which is adapted to receive the signal and, responsive thereto, to transmit information to a computer external to the device.

There is still further provided, in accordance with a preferred embodiment of the present invention, a device for regulating a substance in the body of a subject, including:

an analysis unit, which is adapted to receive a portion of a body fluid of the subject, to analyze the portion, and to generate a signal, responsive to an actual level of the substance in the portion;

a material storage unit, which is adapted to store two or more different material in respective regions of the material storage unit;

one or more electrodes, which are adapted to be placed at respective sites on the skin; and a material delivery unit, which is adapted to receive the signal, and, responsive thereto, to drive the one or more electrodes to apply current to the respective sites on the skin capable of facilitating delivery of one or more of the materials from the storage unit through the skin at the respective sites, so as to maintain a desired level of the substance in the body of the subject.

For some applications, the device includes a transport facilitation unit, adapted to facilitate transport of the portion through the skin. Alternatively or additionally, the device includes a transport facilitation unit, adapted to facilitate transport of one of the substances through the skin.

Preferably, the material delivery unit is adapted to configure the current, responsive to the signal, so as to facilitate delivery of the material stored in one of the regions, while substantially not facilitating the delivery of the material stored in another one of the regions.

There is also provided, in accordance with a preferred embodiment of the present invention, a device for analyzing an analyte extracted through skin of a subject, including:

a housing;

one or more electrodes, fixed to the housing, which one or more electrodes are adapted to be placed at respective sites on the skin;

a control unit, fixed to the housing, which control unit is adapted to drive at least some of the one or more electrodes to apply a current to the respective sites on the skin capable of ablating stratum corneum epidermidis of the skin, so as to facilitate extraction of the analyte through the skin; and an analysis unit, fixed to the housing, which is adapted to analyze the analyte and to generate a signal responsive to the analysis of the analyte.

For some applications, the control unit is adapted:

to designate at a first time a first number of the one or more electrodes to drive to apply the current, responsive to a desired extraction rate of the analyte during a first time period, and to designate at a second time a second number of the one or more electrodes to drive to apply the current, responsive to a desired extraction rate of the analyte during a second time period, the second number being different from the first number.

In a preferred embodiment, the control unit is adapted to:

drive a first subset of the one or more electrodes to apply, during a first time period, a current capable of ablating stratum corneum in a vicinity of the first subset of the one or more electrodes, and drive a second subset of the one or more electrodes to apply, during a second time period, a current capable of ablating stratum corneum in a vicinity of the second subset, wherein the second subset includes at least one electrode which is not in the first subset.

Preferably, the device includes a sensor, adapted to measure a physiological parameter of the subject and to generate a sensor signal responsive thereto, wherein the control unit is adapted to designate the first and second times responsive to the sensor signal.

For some applications, the control unit is adapted to drive a subset of the one or more electrodes to apply:

during a first time period, a current capable of ablating stratum corneum in a vicinity of the subset of the one or more electrodes, and during a second time period, a current capable of ablating stratum corneum in the vicinity.

In a preferred embodiment, the device includes a sensor, adapted to measure a physiological parameter of the subject and to generate a sensor signal responsive thereto, wherein the control unit is adapted to drive the at least some of the one or more electrodes to apply the current responsive to the sensor signal. For example, the sensor may be adapted to measure a physiological parameter selected from the list consisting of: transepidermal water loss (TEWL), a property of the skin, temperature, blood pressure, heart rate, and respiration rate.

Typically, the device includes:

a substance storage unit, which is adapted to store a substance; and a substance delivery unit, which is adapted to receive the signal generated by the analysis unit, and, responsive thereto, to drive a subset of the one or more electrodes to apply a substance-delivery-unit current to respective ones of the sites on the skin so as to facilitate delivery of the substance from the storage unit through the skin at the respective ones of the sites.

There is additionally provided, in accordance with a preferred embodiment of the present invention, a method for delivering a substance to skin of a subject, including:

sensing a physiological parameter of the subject;

analyzing the parameter; and responsive to the analysis of the parameter, applying to the skin a current capable of ablating stratum corneum epidermidis of the skin, so as to facilitate delivery of the substance into the skin.

There is yet additionally provided, in accordance with a preferred embodiment of the present invention, a method for analyzing an analyte extracted through skin of a subject, including:

applying to the skin a current capable of ablating stratum corneum epidermidis of the skin, so as to facilitate extraction of the analyte through the skin;

analyzing the analyte in a device that is attached by the subject to the skin; and responsive to the analysis, transmitting information to a computer external to the device.

There is still additionally provided, in accordance with a preferred embodiment of the present invention, a method for regulating a substance in the body of a subject, including:

storing two or more different materials in respective regions of a material storage unit;

sensing a physiological parameter of the subject;

analyzing the parameter to obtain an indication of an actual level of the substance in the body of the subject;

selecting a material from the two or more materials, responsive to the analysis; and applying to skin of the subject a current capable of facilitating delivery of the selected material from the storage unit into the skin, so as to maintain a desired level of the substance in the body of the subject.

There is also provided, in accordance with a preferred embodiment of the present invention, a device for facilitating transdermal passage of a substance through skin of a subject, including:

one or more electrodes, which are adapted to be placed at respective sites on the skin;

a control unit, which is adapted to drive at least some of the one or more electrodes to apply to respective ones of the sites on the skin a current capable of ablating stratum corneum epidermidis of the skin; and a transport facilitation unit, adapted to facilitate transdermal passage of the substance through an ablated region of the stratum corneum.

For some applications, the transport facilitation unit includes a pressure generation unit, which is adapted to generate a pressure in a vicinity of the skin capable of facilitating the transport of the substance through the skin. In a preferred embodiment, the device includes a storage unit, adapted to store the substance, and the pressure generation unit is adapted to generate a positive pressure capable of facilitating the delivery of the substance from the storage unit through the skin. Alternatively or additionally, the pressure generation unit is adapted to generate a negative pressure capable of facilitating extraction of the substance through the skin.

For further applications, the transport facilitation unit includes a mechanical vibration unit, which is adapted to generate vibrations in the skin capable of facilitating the transport of the substance through the skin. In a preferred embodiment, the device includes a storage unit, adapted to store the substance, and the mechanical vibration unit is adapted to generate vibrations capable of facilitating delivery of the substance from the storage unit through the skin. Alternatively or additionally, the mechanical vibration unit is adapted to generate vibrations capable of facilitating extraction of the substance through the skin.

For yet further applications, the transport facilitation unit includes an ultrasound generation unit, which is adapted to generate ultrasound waves in a vicinity of the skin capable of facilitating transport of the substance through the skin. In a preferred embodiment, the device includes a storage unit, adapted to store the substance, and the ultrasound generation unit is adapted to generate the ultrasound waves so as to facilitate delivery of the substance from the storage unit through the skin. Alternatively or additionally, the ultrasound generation unit is adapted to generate the ultrasound waves so as to facilitate extraction of the portion of the body fluid through the skin.

There is further provided, in accordance with a preferred embodiment of the present invention, a device for facilitating transdermal passage of a substance through skin of a subject, including:

one or more electrodes, which are adapted to be placed at respective sites on the skin; and a control unit, which is adapted:

to drive at least some of the one or more electrodes to apply to respective ones of the sites on the skin a current capable of ablating stratum corneum epidermidis of the skin, so as to facilitate transdermal passage of the substance through the skin, to designate at a first time a first number of the one or more electrodes to drive to apply the current, responsive to a desired rate of passage of the substance during a first time period, and to designate at a second time a second number of the one or more electrodes to drive to apply the current, responsive to a desired rate of passage of the substance during a second time period, the second number being different from the first number.

Preferably, the control unit is adapted to drive the current as an alternating current (AC), e.g., having a frequency of the current to be between about 1 kHz and about 300 kHz.

Typically, the control unit is adapted to drive the current that is capable of causing ablation during a first time period, so as to facilitate passage of the substance through an ablated area of the stratum corneum during a second time period, subsequent to the first time period.

There is yet further provided, in accordance with a preferred embodiment of the present invention, a device for facilitating transdermal passage of a substance through skin of a subject, including:

one or more electrodes, which are adapted to be placed at respective sites on the skin; and a control unit, which is adapted:

to drive a first subset of the one or more electrodes to apply during a first time period, a current capable of ablating stratum corneum in a vicinity of the first subset of the one or more electrodes, so as to facilitate transdermal passage of the substance through the skin, and to drive a second subset of the one or more electrodes to apply, during a second time period, a current capable of ablating stratum corneum in a vicinity of the second subset, so as to facilitate transdermal passage of the substance through the skin, wherein the second subset includes at least one electrode which is not in the first subset.

In a preferred embodiment, the control unit is adapted to drive the current that is capable of causing ablation during the first time period, so as to facilitate passage of the substance through an ablated area of the stratum corneum during a substance-passage time period subsequent to the first time period.

There is still further provided, in accordance with a preferred embodiment of the present invention, a device for facilitating transdermal passage of a substance through skin of a subject, including:

one or more electrodes, which are adapted to be placed at respective sites on the skin; and a control unit, which is adapted to drive a subset of the one or more electrodes to apply:

during a first time period, a current capable of ablating stratum corneum in a vicinity of the subset of the one or more electrodes, and during a second time period, a current capable of ablating stratum corneum in the vicinity of the subset of the one or more electrodes.

The present invention will be more fully understood from the following detailed description of the preferred embodiments thereof, taken together with the drawings in which:

BRIEF DESCRIPTION OF THE DRAWINGS

FIGS. 12A and 12B are schematic illustration of two sides of an electronic drug delivery card, in accordance with a preferred embodiment of the present invention;

DETAILED DESCRIPTION OF PREFERRED EMBODIMENTS

Figure 1A:
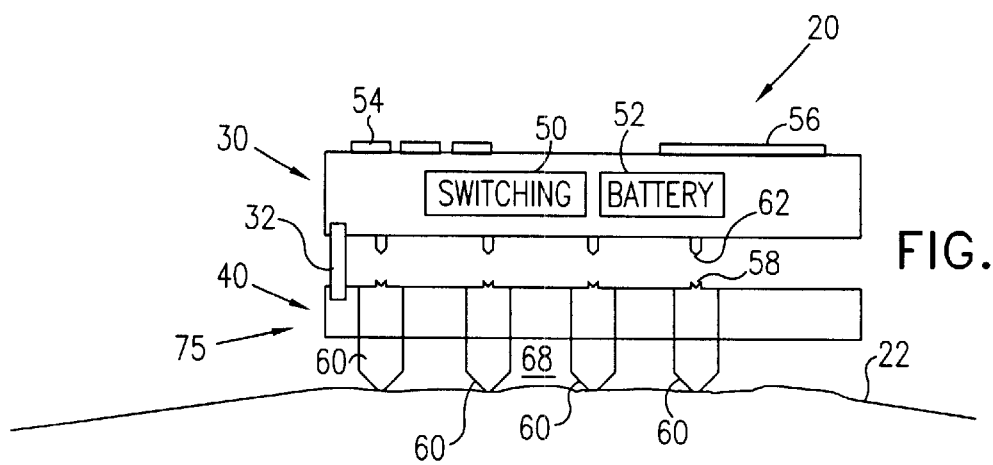
FIG. 1A is a schematic, partly sectional illustration of a device for transdermal transport of a substance, in accordance with a preferred embodiment of the present invention.

FIG. 1A is a schematic, partly sectional illustration of a skin puncturing device 20 for transdermal delivery of an active substance and/or transdermal extraction of an analyte, in accordance with a preferred embodiment of the present invention. Device 20 comprises a control unit 30 attached to a skin patch 40, which is preferably fixed to a suitable area of a subject's skin 22. Device 20 preferably administers an active substance through the normally substantially-impermeable stratum corneum layer of the skin by passing a controlled electric current therethrough, thereby ablating the stratum corneum and generating micro-channels through which the substance can pass. Alternatively or additionally, device 20 is used to generate micro-channels in the stratum corneum in order to allow passage of molecules to patch 40 from the underlying tissue, generally for diagnostic purposes.

When device 20 drives current through the stratum corneum, this tissue is heated resistively, so that when a sufficient quantity of energy has passed therethrough in a short time period, the tissue is ablated by the total energy dissipated therein. This ablation creates the desired micro-channels, i.e. physical gaps in the tissue. It has been found that application of a current to a small area of the skin leads to formation of such micro-channels, through which even large molecules can pass relatively freely, without the necessity of ionizing or polarizing the molecules, and without causing pain or substantial trauma to the dermis and epidermal tissue underlying the stratum corneum.

Control unit 30 preferably comprises a switching unit 50, a battery 52 (such as a lithium coin cell battery), and an optional user-interface comprising buttons 54 and a sensible signal generator 56, which may comprise a display and/or a buzzer. In a simplest embodiment, buttons 54 initialize and terminate analyte extraction or delivery of the active substance, although buttons 54 preferably also programmably control extraction or dosage rate and duration.

Patch 40 comprises two or more electrodes 60, preferably an array 75 of electrodes, which pass current into and out of the skin. In applications of device 20 for transdermal drug delivery, when a micro-channel has formed responsive to current flow between the electrodes, the active substance stored in patch 40 flows therethrough. In the patch, the active substance is preferably stored in or applied to inter-electrode regions 68 and flows directly therefrom into the micro-channels created in the skin.

Control unit 30, containing switching unit 50 and battery 52, is preferably designed for repeated use, to be removably attached to disposable skin patch 40. Before use, control unit 30 is fitted onto patch 40, and a protective tab (not shown) on the lower surface of patch 40 is preferably removed, exposing the one or more electrodes 60, and, in drug delivery systems, the active substance. One or more optional alignment pins 32 are preferably incorporated into control unit 30 and/or skin patch 40 to maintain proper alignment therebetween. Fitting control unit 30 to patch 40 also couples electrical contacts 62 on a lower surface of control unit 30 with electrical contacts 58 on an upper surface of skin patch 40. In some other preferred embodiments of the present invention (not shown), control unit 30 and skin patch 40 are constructed as one integrated unit.

Figure 1B:
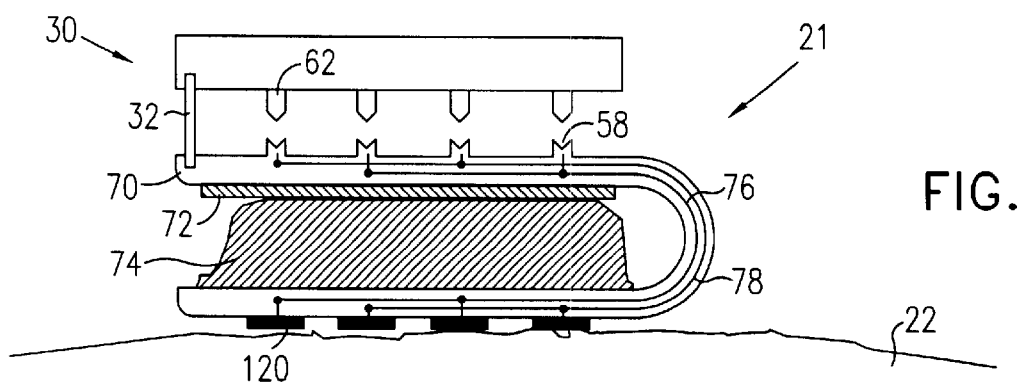
FIG. 1B is a schematic, partly sectional illustration of another device for transdermal transport of a substance, in accordance with a preferred embodiment of the present invention.

FIG. 1B is a schematic, partly sectional illustration of another device 21 for transdermal transport of a substance, in accordance with a preferred embodiment of the present invention. Device 21 operates in substantially the same manner as device 20, described hereinabove, but device 21 is preferably used in an add-on configuration with commercially available medical patches. Typically, a medical patch 74 is coupled to a porous, thin, flexible, and disposable electrode patch 70, which is used to create micro-channels in skin 22 so as to enable enhanced flow of an active substance stored within medical patch 74 through electrode patch 70 and into skin 22.

Electrode patch 70 is preferably constructed such that electrical contacts 58 thereof are coupled to electrical contacts 62 of control unit 30 and carry charge through flexible leads 76 and 78 internal to patch 70, in order to create an electric field between electrodes 120 placed against the surface of skin 22. Prior to use, medical patch 74 is placed onto electrode patch 70, typically on the opposite side of patch 70 from electrodes 120. An adhesive on the underside of medical patch 74 preferably secures the two patches together. Subsequently, electrode patch 70 is folded over, as shown in FIG. 1B, such that an upper surface of patch 74 is secured through an adhesive 72 to electrode patch 70. During operation of device 21, the active substance preferably diffuses from the lower surface of patch 74 into, and then through, patch 70 into skin 22. Device 21 is thus compatible with a broad range of currently available active or passive medical patches, which are typically of the same general construction (thin shell, internal reservoir of active substance, porous and adhesive-coated undersurface).

It is understood, of course, that device 21 as described is only one of many ways to implement some aspects of the present invention. Alternatively, for example, electrode patch 70 is not folded over; instead, control unit 30 is placed next to medical patch 74 on top of electrode patch 70. Further alternatively, control unit 30 has electrical contacts on its upper surface to which are coupled the electrical contacts of the electrical patch.

Figure 2:
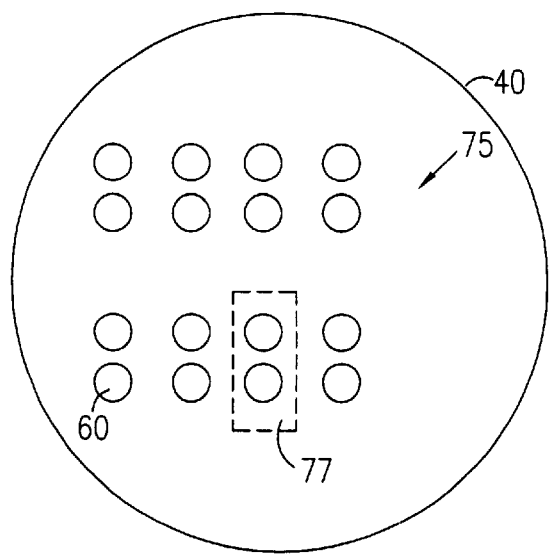
FIG. 2 is a schematic bottom view of the device of FIG. 1A, in accordance with a preferred embodiment of the present invention.

FIG. 2 is a schematic bottom view of skin patch 40 from FIG. 1A, showing array 75 of electrodes 60, in accordance with a preferred embodiment of the present invention. Although array 75 as shown comprises sixteen electrodes, it is understood that in some implementations the array might be smaller, while in others the array might be larger, for example 50×50 or even more, so as to enable a greater amount of the active substance to be delivered or analyte to be extracted. Electrodes 60 in this embodiment are preferably organized into eight electrode sets 71, such that most of the charge leaving one electrode in a set goes to the other electrode in that set, and generally does not go to electrodes in an adjacent set. Electrode sets 77 are further preferably densely packed in order to maximize the transdermal transfer rate. By way of illustration and not limitation, the density may range from 4–100 electrode sets/cm$^2$. Each electrode set typically generates at least one micro-channel before a threshold of current or total charge transfer is passed, responsive to which switching unit 50 preferably causes current to the electrode set to be terminated or reduced, as described herein.

Figure 3:
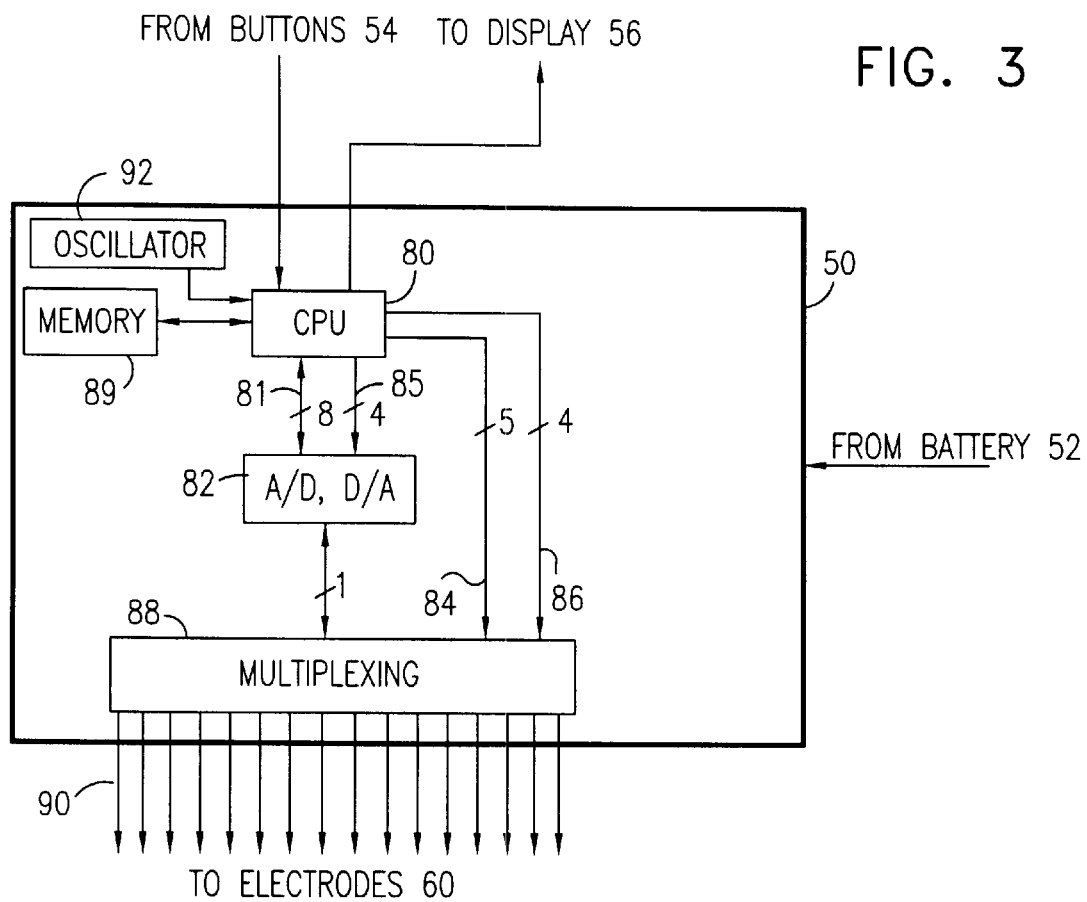
FIG. 3 is a schematic illustration of a switching unit in the device of FIG. 1A, in accordance with a preferred embodiment of the present invention.

FIG. 3 is a schematic illustration of switching unit 50 in device 20 of FIG. 1A, configured to control a 4×4 array of electrodes 60, as in FIG. 2, in accordance with a preferred embodiment of the present invention. Switching unit 50 preferably comprises a CPU 80 which actively controls the voltage V(t) applied to sixteen conductors 90 leading to electrodes 60. CPU 80 monitors the current flow, I(t), through each of conductors 90 leading to electrodes 60 in order to determine whether a characteristic of the current (e.g., time-integrated current, I, dI/dt, d$^2$I/dt$^2$) has surpassed a threshold, indicating micro-channel formation. The CPU terminates current flow to any electrode for which the threshold has been surpassed. Alternatively or additionally, in some applications, some of electrodes 60 are generally not used to initiate channel formation, but serve primarily to allow CPU 80 and/or other circuitry to monitor electrical properties of skin 22.

CPU 80, which receives a clock signal from an oscillator 92, preferably communicates with and controls electrodes 60 through eight data lines 81 and four control lines 65 which lead to an A/D-D/A converter 82, and by five address lines 84 and four control lines 86 which lead to a multiplexing unit 88. It will be understood by one skilled in the art that there are many methods to monitor and control current through a plurality of conductors, and that using a CPU, A/D-D/A converter and multiplexing unit as described herein is just one of these. Generally, data lines 81 carry in alternation a low byte and a high byte of data between the CPU and A/D-D/A converter 82. Typically, 10 bits of data, representing a desired voltage for one of the sixteen electrodes, are converted to an analog voltage in A/D-D/A converter 82, and this voltage is passed by multiplexing unit 88 to an appropriate electrode, the electrode selection being determined by the binary values represented in address lines 84. In many applications, fewer than 10 bits are required to define voltages for the respective electrodes, and circuitry within switching unit 50 is accordingly simpler.

Intermittently, CPU 80 enters a current sensing mode, wherein switching unit 50 continues to drive current through conductors 90, but the CPU changes the state of control lines 85 and 86 in order to measure the current flow through conductors 90. Responsive to the change in control lines 86, multiplexing unit 88 measures a current through one of conductors 90, converts this measurement to a voltage, and passes the voltage to A/D-D/A converter 82 which in turn passes the digital value representing the current to the CPU.

Preferably, CPU 80 scans through each of the sixteen electrodes, detects a present current flow value, stores this value in an optional memory unit 89, optionally compares the value with prior values for the same electrode in order to calculate $\int I(t)dt$, dI/dt and/or d$^2$I/dt$^2$, and regulates the potential of that electrode responsive to the current measurement and/or optional calculation. It will be understood by one skilled in the art that CPU 80, oscillator 92, and memory 89 could be replaced by other circuitry able to perform generally the same functions.

Figure 4:
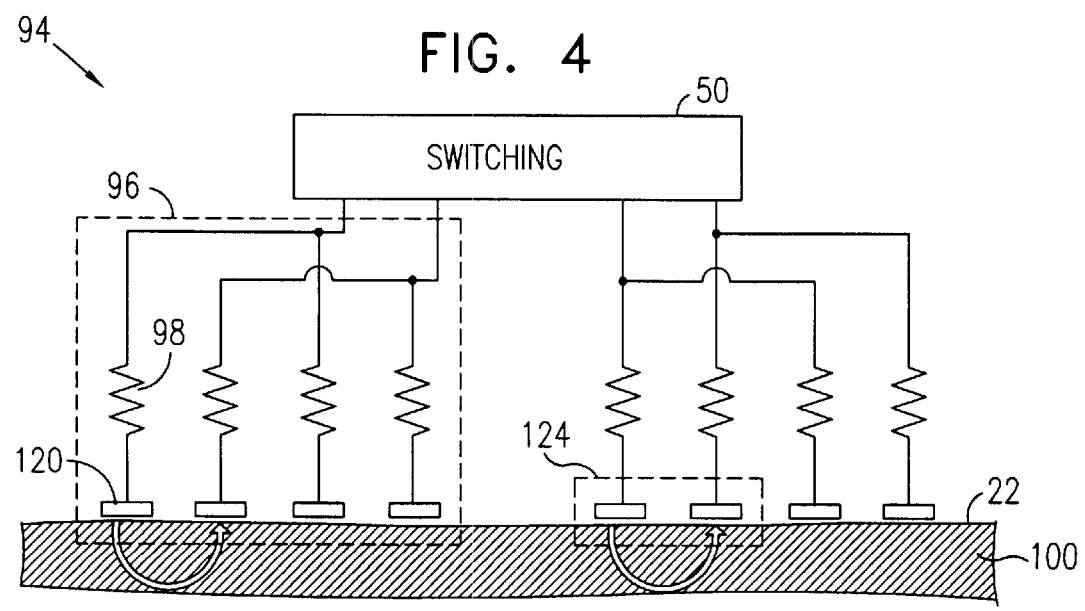
FIG. 4 is a schematic illustration of an electrode assembly, in accordance with a preferred embodiment of the present invention.

FIG. 4 is a schematic illustration of an electrode assembly 94, comprising a plurality of electrodes 120, which are placed on skin 22 in order to generate micro-channels in the stratum corneum 100, in accordance with a preferred embodiment of the present invention. Electrodes 120 in assembly 94 are grouped in sometimes overlapping sets of two or more electrodes, forming a plurality of electrode sets 124, one of which is indicated with a dashed line in FIG. 4. Current, coming from switching unit 50, generally flows from one electrode in each electrode set to the other electrodes of the set. An arrow going between the two electrodes in set 124 indicates the preferred flow of current.

Preferably, the spacing between electrodes in each electrode set is smaller than about 0.1 mm, although for some applications it may range from (by way of illustration and not limitation) 0.1 mm to about 0.3 mm. Generally, the distance is set such that an electric field penetration depth is achieved which is substantially of the same magnitude as the thickness of the stratum corneum, so that the current mostly does not enter epidermal tissue underlying the stratum corneum. Experimental results have shown that the depth of deepest ablation is generally similar to the electrode spacing, so maintaining the spacing between about 0.01 mm and about 0.1 mm optimizes generation of micro-channels while substantially reducing damage, sensation and/or pain in the innervated dermis and in the epidermal tissue below the stratum corneum.

At any point in the skin in a vicinity of two electrodes placed thereon, the electric field generated between the electrodes can be viewed as having fundamentally two components: a component perpendicular to the skin, which generally causes current flow perpendicular to the skin; and a lateral component, which generally causes current flow parallel to the skin. At a point in the skin infinitesimally below one of the electrodes, the perpendicular component is generally large and/or greater than the lateral component. The present invention seeks generally to maximize the ratio of the lateral component to the perpendicular component at the depth corresponding to the interface between the deepest portion of the stratum corneum and the most superficial portion of the remainder of the epidermis. An electric field at the base of the stratum corneum having a relatively large lateral component generates current flow predominantly in the stratum corneum, with relatively little current flow into the underlying epidermal tissue. Thus, using methods and apparatus of the present invention, tissue ablation occurs mostly in the stratum corneum, as desired, and largely does not occur in the underlying tissue.

In some applications of the embodiment shown in FIG. 4, it is preferred to print electrodes 120 directly on skin 22, typically (a) by stamping the electrodes thereon; (b) by employing a transfer patch of a conductive substance; and/or (c) by other techniques known in the art. Switching unit 50 preferably sends current to the printed electrodes via printed ports (not shown) on the upper surface of the electrodes. In uses of the present invention for transdermal drug delivery, the conductive substance preferably contains an active substance, typically dissolved or suspended therein. Alternatively or additionally, it is desirable for the printed electrode to disconnect from the switching unit or power source at substantially the same time as ablation of the stratum corneum is completed. This "self-quenching" feature of the printed electrodes is typically achieved by controlling fabrication of the electrodes, in particular by regulating the thickness and/or chemical composition thereof. Printed electrodes comprising a silver-based emulsion ink preferably undergo thermal fusion within the ink responsive to high current flow, resulting in a decrease in electrical conduction therethrough.

As discussed hereinabove with reference to FIG. 3, switching unit 50 monitors current flow to electrodes 60 (or electrodes 120, shown in FIG. 1B and subsequent figures), and selectively terminates the flow to one or more electrodes upon a determination that ablation of stratum corneum 100 has occurred. Making reference to FIG. 4, a cluster 96 of electrodes is a grouping of electrodes 120, which are typically in very close mutual proximity, and are therefore assumed to overlie an area of skin 22 which has generally uniform properties. By way of illustration and not limitation, cluster sizes generally range from about 4 mm$^2$ to about 100 mm$^2$. Switching unit 50 preferably monitors and terminates the current flow through the electrodes in cluster 96 collectively (i.e. for all of the electrodes, not individually for each electrode). Alternatively or additionally, current through electrodes 120 in cluster 96 is determined by monitoring the current in only a subset of the electrodes, and assuming the value derived therefrom to be generally representative of current through each of the other electrodes. Upon a determination by switching unit 50 that stratum corneum 100 under cluster 96 has been ablated, the current flow to all of the electrodes in cluster 96 is substantially terminated. Monitoring of clusters of electrodes generally simplifies control circuitry associated with the invention, while not substantially decreasing the performance thereof.

Optional resistive elements 98, coupled in series between switching unit 50 and electrodes 120, limit the power dissipation in the skin following the large increase of conductivity in the epidermis associated with ablation of the stratum corneum. Typical values for resistive elements 98 range from 1 kOhm–100 kOhms, but in some applications may have values outside of this range.

Figure 5:
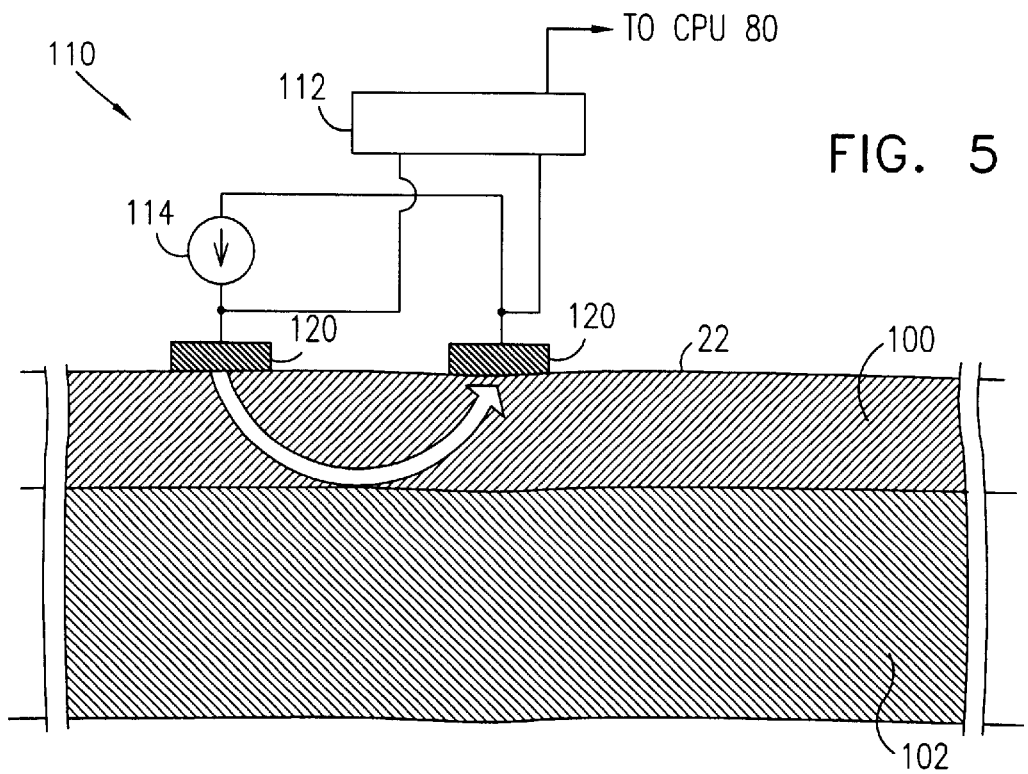
FIG. 5 is a schematic illustration of another electrode assembly, in accordance with a preferred embodiment of the present invention.

FIG. 5 is a schematic illustration of another electrode assembly 110, comprising a current source 114 coupled to drive charge through electrodes 120 on skin 22, in accordance with a preferred embodiment of the present invention. Current source 114 preferably comprises a source of electrical power (for example, a battery) connected in series with an inductive element which, due to pulse charging, exhibits properties of a current source, thereby limiting the power dissipated in underlying epidermal tissue 102 following the drop in resistance of the epidermis associated with substantially complete ablation of stratum corneum 100. Alternatively or additionally, current-limited source 114 comprises active components such as transistors, op-amps, commercially-available "ideal" current sources, etc., which maintain the current through the skin generally constant after ablation of the stratum corneum, so that the power dissipated (P=I$^2$R) will decrease with the reduced resistance of the skin upon the electrical breakdown of stratum corneum 100.

Prior to breakdown, the impedance between electrodes 120 is high, producing a generally large voltage drop therebetween, so the energy dissipated in the skin (P=VI) has a desired high value. The energy dissipation rate is preferably sufficient to cause electrical breakdown of stratum corneum 100 in a short time, which is typically less than 50 milliseconds, but may range from about 1 to about 1000 milliseconds. Reported values of the voltage needed to break down stratum corneum 100 spread over a range of approximately 5–1000 volts. For the purposes of the present invention, it has been found that an inter-electrode voltage of approximately 100 volts generally ablates stratum corneum 100 without causing significant damage to underlying tissue 102. It is understood, however, that for some applications or types of subjects/patients, lower or higher inter-electrode voltages may be more suitable.

Intermittently or continuously during application of the electric field to skin 22, an optional voltage sensing unit 112 preferably measures the interelectrode voltage and sends a signal corresponding thereto to CPU 80 or other circuitry in switching unit 50, which regulates the current produced by source 114 responsive to the signal. Alternatively or additionally, voltage sensing unit 112 comprises a comparator which intermittently or continuously compares the interelectrode voltage to a pre-determined threshold value, and signals source 114 when the voltage is below the threshold. In either case, the CPU, circuitry and/or comparator preferably control source 114 to reduce or terminate current flow responsive to a drop of the interelectrode voltage below the threshold value.

Figure 6:
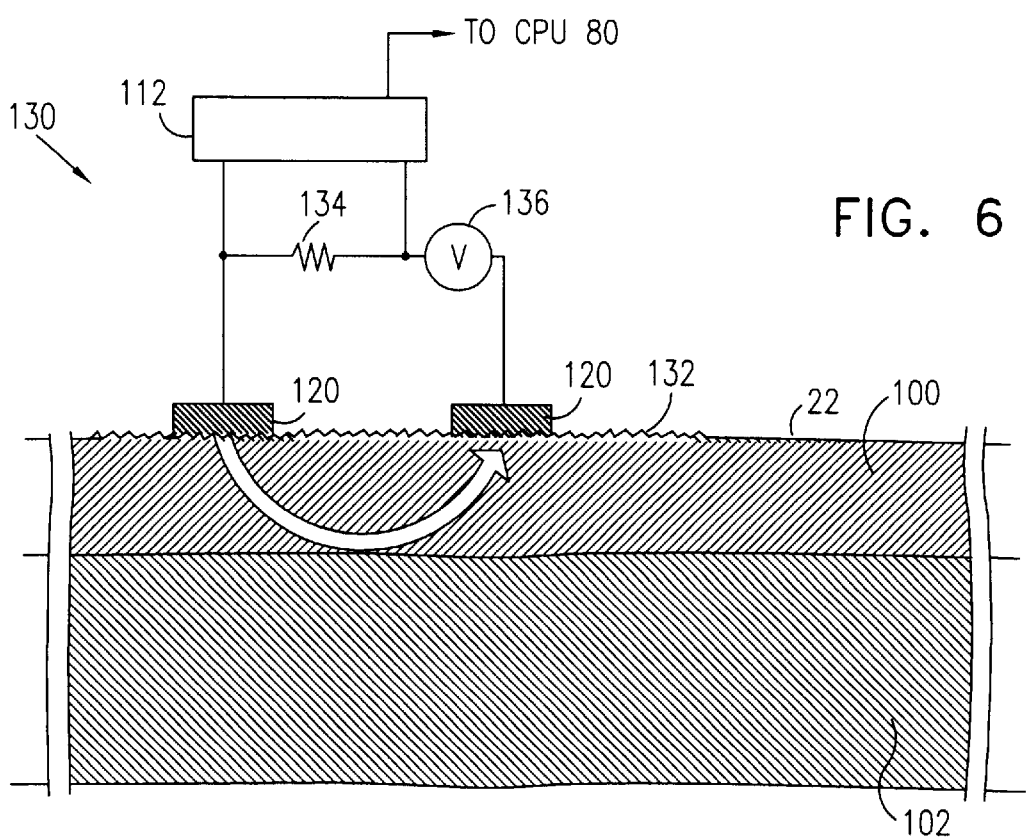
FIG. 6 is a schematic illustration of yet another electrode assembly, in accordance with a preferred embodiment of the present invention.

FIG. 6 is a schematic illustration of another electrode assembly 130, comprising a voltage source 136 coupled in series through an optional resistive element 134 to two electrodes 120 on the surface of skin 22, in accordance with a preferred embodiment of the present invention. Optional voltage sensing unit 112 measures the voltage drop across resistive element 134 in order to determine the current passing therethrough. In a manner substantially similar to that described hereinabove with reference to FIG. 5, unit 112 and/or CPU 80 and/or other circuitry in switching unit 50 regulate the output of voltage source 136 responsive to the measurement made by unit 112. Preferably, when the voltage drop across element 134 exceeds a predetermined threshold value, this is used as an indication of stratum corneum ablation and causes the voltage generated by source 136 to be reduced or terminated responsive thereto.

In applications of the embodiment shown in FIG. 6, if optional resistive element 134 and optional voltage sensing unit 112 are not used, it is preferable to employ other means for significantly reducing the current flow through electrodes 120 after micro-channel formation. This is preferably done by using "self-quenching" printed electrodes, as described hereinabove with reference to FIG. 4.

Alternatively or additionally, a conductivity-enhancing substance 132 is applied to skin 22 prior to placement of electrodes 120 thereon. Substance 132 typically improves current flow into skin 22 by decreasing the electrical resistance at the interface between electrodes 120 and skin 22. Experimental results indicate that use of substance 132 has the additional desired effect of increasing the above-mentioned ratio of the lateral component of the electric field to the perpendicular component thereof. In particular, it is believed that substance 132 diffuses into stratum corneum 100 and reduces the lateral resistance and lateral breakdown strength of the stratum corneum. By virtue of the relationship P=V$^2$/R, the increased conductivity in stratum corneum 100 (prior to the breakdown thereof) deriving from the presence of substance 132 produces a relatively high rate of energy dissipation in the stratum corneum. However, as ablation occurs, it has been observed that the enhanced conductivity path due to substance 132 is substantially removed, resulting in an increase in resistance and the desired attendant decrease in energy dissipation in the skin Substance 132 typically comprises a conductive cream, gel and/or ink. In some applications of this embodiment, substance 132 additionally comprises a material which has a high diffusion coefficient into the skin and promotes the increased lateral component of the electric field relative to the perpendicular component, as described hereinabove. Alternatively or additionally, "pre"-iontophoresis, using a relatively weak electric field, is used to enhance the flow of substance 132 into the outer layer of the skin before application of the stronger electric fields which create the micro-channels. The presence of the conductive substance in the skin subsequent to the pre-iontophoresis is believed to increase the rate of micro-channel creation. Pre-iontophoresis is typically implemented by applying, for example, a 3 volt DC field between the electrodes for 30 seconds in order to drive substance 132 into the skin. Alternatively or additionally, a larger AC current which produces micro-channels is supplemented by a simultaneous small DC current which supports iontophoresis of substance 132 and thereby enhances micro-channel creation.

In some applications, when micro-channels are created in order to enhance transdermal delivery of an active substance, the active substance is preferably incorporated in substance 132.

Figure 7:
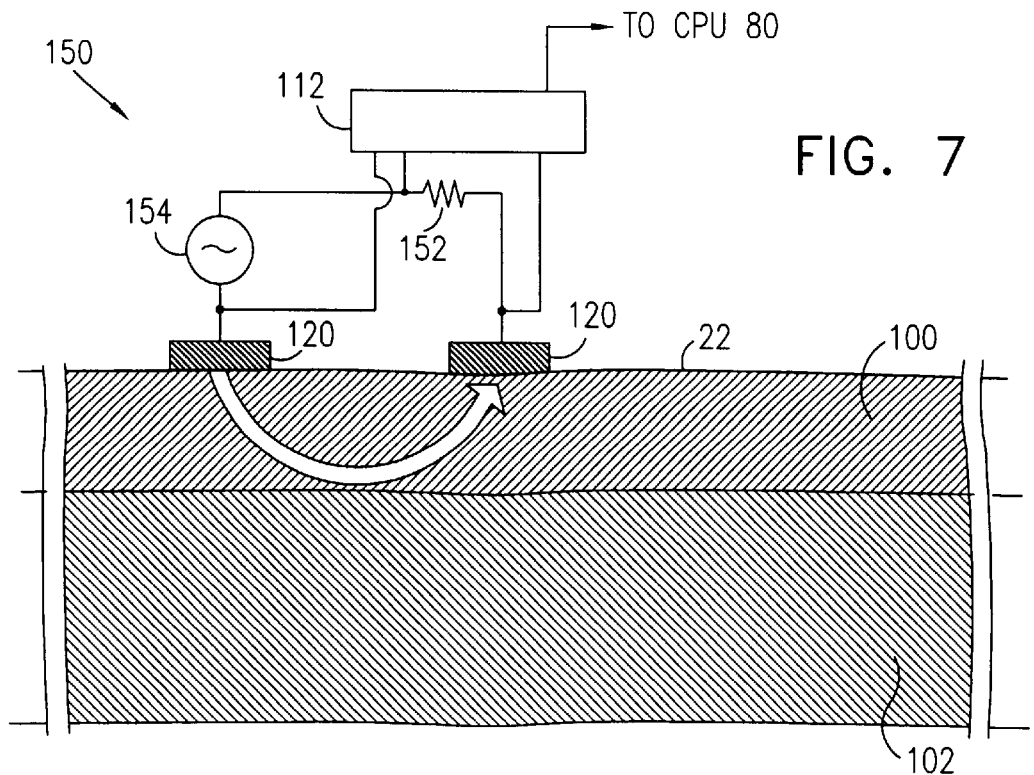
FIG. 7 is a schematic illustration of still another electrode assembly, in accordance with a preferred embodiment of the present invention.

FIG. 7 is a schematic illustration of another electrode assembly 150, comprising an AC current source 154 coupled in series with an optional resistive element 152 in order to drive current through electrodes 120 and skin 22, in accordance with a preferred embodiment of the present invention. It has been reported that the driving frequency of current through skin has a significant effect on the sensation or pain experienced by a subject. See, for example, *Principles of Applied Biomedical Instrumentation,* by L. Geddes and L. Baker, John Wiley & Sons, 1989, which is incorporated herein by reference. For the purposes of the present invention, a 10 kHz driving frequency has been found to yield good results, although any frequency between about 100 Hz and about 10 MHz is appropriate for most applications. Depending on properties of a subject's skin, it is sometimes appropriate to use driving frequencies outside of this range. Optionally, the driving frequency is cyclically modulated between two endpoints (e.g., 2 kHz and 15 kHz) during application of the electric field, such that a graph representing frequency versus time (not shown) is typically sinusoidal or triangular in character.

Stratum corneum 100 generally displays properties of a simple insulator when exposed to DC current, but displays significant capacitance under AC stimulation, particularly when the driving frequency is above 1 kHz. At these frequencies, current flow through the stratum corneum dissipates energy therein, contributing to the heating and ultimate ablation of the stratum corneum. The pre-ablation capacitance produces a measurable phase shift between the voltage across the electrodes and the current flowing therebetween, which phase shift is seen to be significantly reduced upon commencement and completion of the ablation of the stratum corneum. Sensing unit 112 is typically used to detect this phase shift by measuring the inter-electrode voltage, as described hereinabove, and by determining the current flow through electrodes 120, preferably by measuring the voltage drop across optional resistive element 152. The change of the phase shift from baseline is preferably used by sensing unit 112 and/or CPU 80 and/or other circuitry in switching unit 50 to indicate breakdown of the stratum corneum, responsive to which current flow to electrodes 120 demonstrating such a change preferably is reduced or terminated.

As described hereinabove, in some applications, substance 132 is applied to skin 22, and a DC current is superimposed on the AC current in order to cause iontophoresis of substance 132 during micro-channel creation.

Alternatively or additionally, in applications using AC and/or DC current delivery (as in FIGS. 5, 6 and 7), the duration of charge delivery is limited by means of an optional ordinary timer circuit (not shown). Further alternatively or additionally, the total charge delivered (or root mean squared charge in AC operation modes) is limited using methods known in the art. For example, energy storage components such as capacitors and/or inductors can be used to modulate charge delivery.

Although in the embodiments shown in FIGS. 5, 6, and 7, passing a threshold of current or voltage is used as an indicator of when to reduce the current applied to the skin, other functions of the current and/or voltage, such as derivatives, time-integrals, and/or powers thereof may also be evaluated in order to determine when the current should be reduced.

Figure 8A:
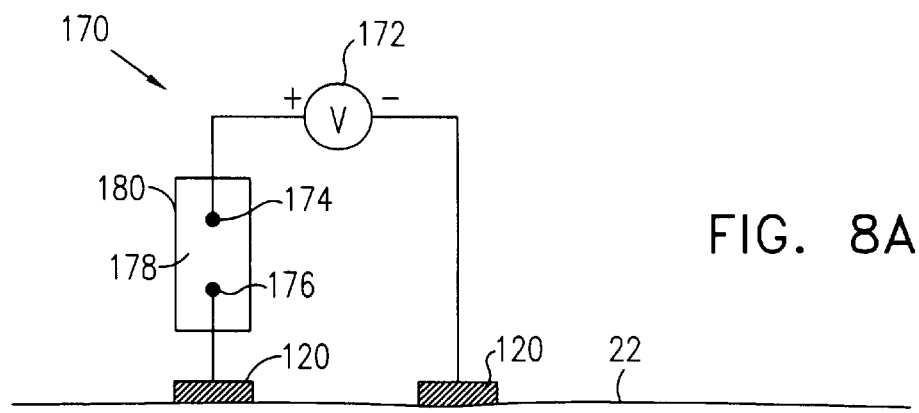
FIGS. 8A and 8B are schematic illustrations of charge-limited electrode assemblies, in accordance with preferred embodiments of the present invention.

FIG. 8A is a schematic illustration of a charge-limited electrode assembly 170, comprising an electrolyte cell 180 connected in series between a power source 172 and electrodes 120, in accordance with a preferred embodiment of the present invention. Electrolyte cell 180 comprises an anode 174 and a cathode 176, both immersed in an electrolyte solution 178, which acts as a medium for current flow from anode 174 to cathode 176. As current flows through cell 180, cathode 176 is steadily consumed by electrolysis until electrolyte cell 180 becomes substantially non-conductive. In this manner, consumption of cathode 176 progresses at a rate which is generally proportional to the current flowing therethrough. By modifying the initial mass of cathode 176, cell 180 can be built to allow a flow of charge that substantially does not exceed a predetermined value.

Figure 8B:
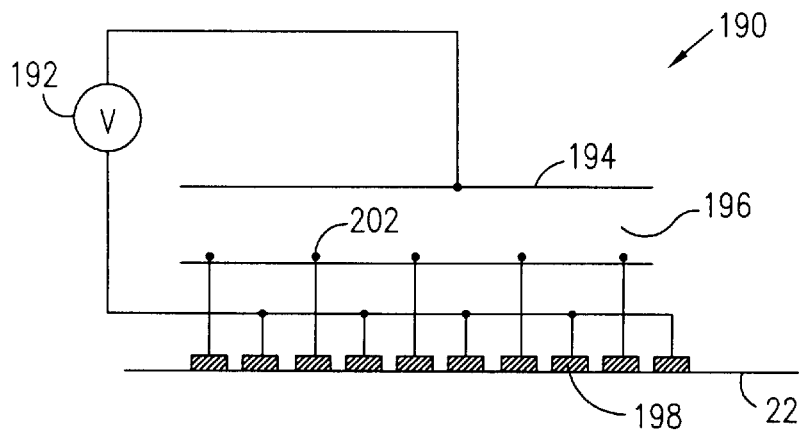

FIG. 8B is a schematic illustration of another charge-limited electrode assembly 190, comprising a power source 192 which sends current to a large-area anode 194 from which it flows through an electrolyte solution 196 to multiple cathodes 202, in accordance with a preferred embodiment of the present invention. In general, the charge-limiting functions embodied in assembly 190 are similar to those described with respect to the embodiment shown in FIG. 8A. Anode 194 comprises a fibrous material, such as paper, having fibers aligned in a generally vertical direction, perpendicular to the surface of skin 22. Alternatively or additionally, anode 194 is in very close proximity to cathodes 202, typically from about 0.1 mm to about 2 mm, in order to enhance independent termination of current through electrodes 198 coupled to cathodes 202, by reducing lateral conduction within the electrolyte solution.

Figure 9:
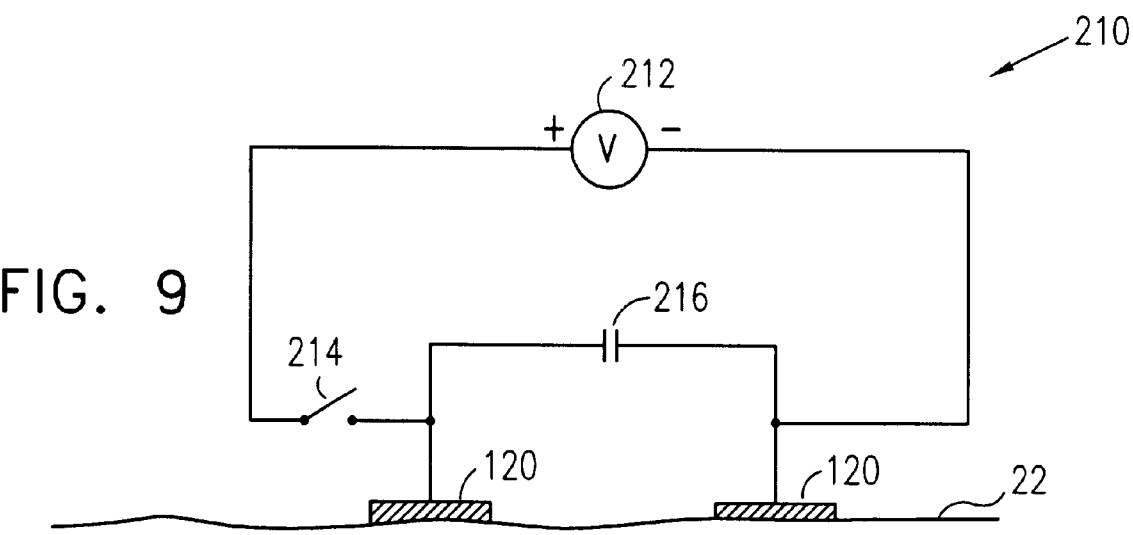
FIG. 9 is a schematic illustration of another charge-limited electrode assembly, in accordance with a preferred embodiment of the present invention.

FIG. 9 is a schematic illustration of yet another charge-limited electrode assembly 210, comprising a power source 212 in series with a controlled switch 214, in accordance with a preferred embodiment of the present invention. Source 212 and switch 214 are connected in series with a capacitor 216 across electrodes 120, which are applied to skin 22. Capacitor 216 is preferably utilized in order to limit the total charge delivered through electrodes 120 to generally not more than the charge-holding capacity of capacitor 216 at a designated voltage generated by source 212, given by the formula $q=CV$, wherein C is the capacitance of the capacitor. By way of illustration and not limitation, for an applied voltage of 50 volts, a capacitor whose capacitance ranges from about 1 nF to about 0.2 µF is appropriate.

A typical operational sequence in this preferred embodiment comprises: (a) turning on source 212; (b) closing switch 214, which results in substantially all of the current from source 212 going through and charging low-impedance capacitor 216; (c) opening switch 214 and turning off source 212; (d) allowing the discharge from capacitor 216 to drive the ablation of the stratum corneum; and (e) passively terminating the process responsive to complete discharge of capacitor 216.

Figure 10:
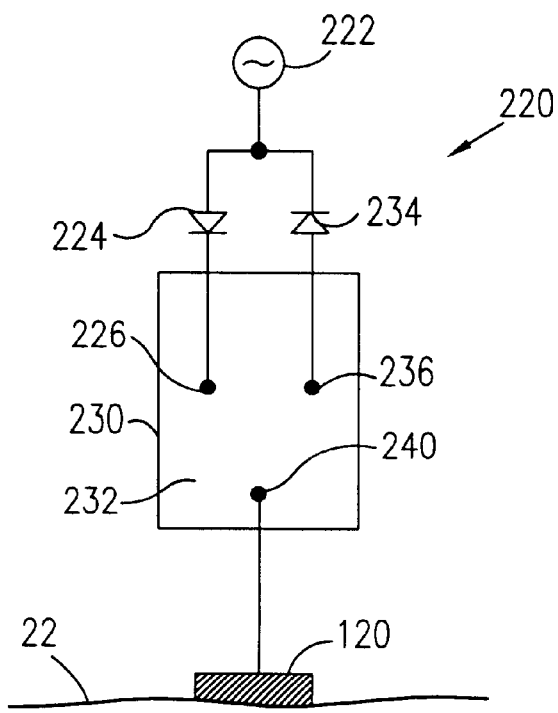
FIG. 10 is a schematic illustration of yet another charge-limited electrode assembly, in accordance with a preferred embodiment of the present invention.

FIG. 10 is a schematic illustration of still another charge-limited electrode assembly 220, comprising an AC source 222 coupled in series to an electrolyte cell 230, electrode 120, and skin 22, in accordance with a preferred embodiment of the present invention. Cell 230 preferably comprises two alternating nodes 226 and 236 and a common node 240, all nodes being immersed in an electrolyte solution 232. Except as will be described below, the function of electrolyte cell 230 is substantially similar to that of electrolytic charge-limiting devices described hereinabove with reference to FIGS. 8A and 8B.

AC source 222 produces a voltage difference across electrodes 120 (only one electrode is shown), which cycles between positive and negative phases at a pre-determined frequency, in order to provide the energy to ablate stratum corneum 100 in skin 22. During the positive phase, a diode 224 in electrolyte cell 230 passes current to cause alternating node 226 to act as an anode and common node 240 to act as a cathode, which is subsequently consumed by the electrolysis thereof during each positive phase. Conversely, during the negative phase, diode 224 blocks conduction through alternating node 226, halting the consumption of common node 240 associated with the positive phase. In a similar manner, during the negative phase, a second diode 234 passes current which allows alternating node 236 to act as a cathode (which is consumed) and common node 240 to act as an anode. When a sufficient quantity of charge has passed through electrolyte cell 230, common node 240 is completely consumed, and cell 230 becomes substantially non-conductive. Preferably, the properties of electrolyte cell 230 are determined so chat the cell becomes non-conductive after passing a quantity of charge which correlates with breakdown of the stratum corneum.

Figure 11A:
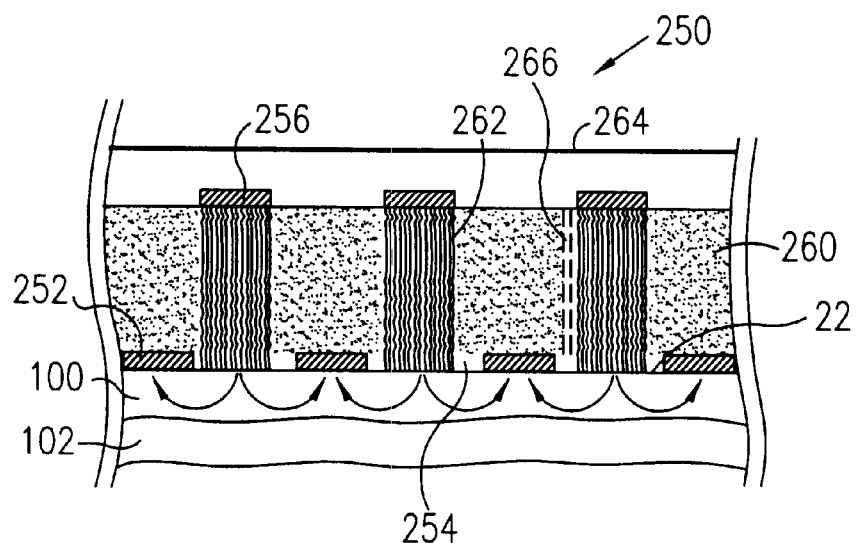
FIG. 11A is a schematic side view of a concentric electrode assembly, in accordance with a preferred embodiment of the present invention.
Figure 11B:
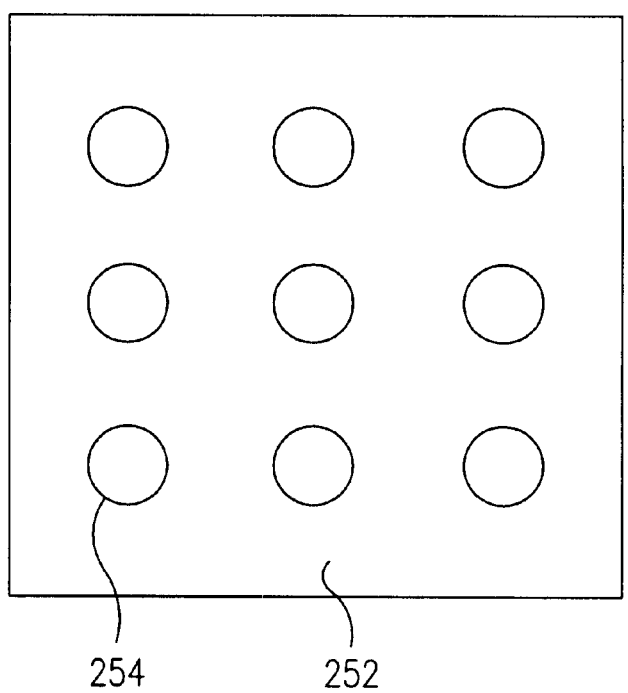
FIG. 11B is a schematic top view of a common electrode layer in the concentric electrode assembly of FIG. 11A, in accordance with a preferred embodiment of the present invention.

Reference is now made to FIGS. 11A and 11B which are, respectively, a schematic side view of a concentric electrode assembly 250 and a schematic top view of a common electrode layer 252 in assembly 250, in accordance with a preferred embodiment of the present invention. A substantially non-conductive substrate 260 overlies common electrode layer 252. Perforations 254 in layer 252 allow passage therethrough of electrodes 262, which receive charge through optional resistive members 256 from a charging bus 264 overlying substrate 260. Electrodes 262, which preferably comprise a plurality of conductive fibers, are electrically coupled to skin 22, and cause charge to pass into skin 22 and subsequently out of skin 22 through common electrode layer 252, in order to ablate stratum corneum 100.

In some preferred applications, one or more pores 266 traversing substrate 260 allow flow of active substances/analytes through substrate 260 from/to a reservoir (not shown) above substrate 260. It is noted that fabrication of concentric electrode assembly 250 is substantially similar to the process of flexible printed circuit production, which is well known in the art.

Reference is now made to FIGS. 12A and 12B. FIG. 12A is a schematic illustration of a skin-contact side 312 of an electronic drug delivery card 300 for transdermal delivery of an active substance, in accordance with a preferred embodiment of the present invention. FIG. 12B is a schematic illustration of the reverse side 310 of card 300, in accordance with a preferred embodiment of the present invention.

It is to be understood that apparatus and methods described hereinabove for ablating stratum corneum may be adapted for use with the embodiments of the present invention described with reference to FIGS. 12A, 12B, 13, and 14. Alternatively or additionally, apparatus and methods described in a U.S. patent application entitled, "Handheld apparatus and method for transdermal drug delivery and analyte extraction," filed Apr. 23, 2001, which is assigned to the assignee of the present patent application and is incorporated herein by reference, may be adapted for use with these embodiments of the present invention, Further alternatively or additionally, apparatus and methods described in a U.S. patent application filed on even date with the present patent application, entitled, "Monopolar and bipolar current application for transdermal drug delivery and analyte extraction," which is assigned to the assignee of the present patent application and is incorporated herein by reference, may be adapted for use with these embodiments of the present invention.

A plurality of electrodes 306 are preferably arranged as an array 304 on the skin-contact side of card 300. The electrodes are typically incorporated into a plurality of linear electrode elements. Fourteen elements are shown in FIG. 12A, each including 26 individual electrodes 306, connected in series. Electrodes 306 are typically equally spaced, with a distance of about 200 microns separating electrodes in adjacent elements. Card 300 preferably comprises drug delivery regions 308, between electrodes 306, in which an active substance is stored until the passive delivery thereof following ablation of the skin by the electrodes. For some applications, card 300 is adapted to provide active transport of the substance into the skin.

Electrodes 306 on skin-contact side 312 of card 300 are preferably coupled to a battery 322 and control unit 320 via electrode connectors 302, which typically fold around an edge of the card, as shown in FIGS. 12A and 12B. Alternatively, electrical current from battery 322, regulated by control unit 320, passes through holes in the card (not shown) to drive electrode array 304.

Preferably, electronic drug delivery card 300 is about the size of a credit card, although it will be appreciated that housings of other shapes and sizes may also be appropriate. Card 300 typically comprises an adhesive around the edge of skin-contact side 312 to facilitate secure coupling of the card to the subject's skin. Additionally, card 300 preferably comprises a cover 324, which protects electrodes 306, drug delivery regions 308, and the adhesive prior to use. Preferably, the subject removes the cover shortly before placing the card on her skin. Although for some applications electronic drug delivery cards may be configured to accept refills of the drug, card 300 is typically discarded following a single treatment or following exhaustion of the active substance.

Figure 13:
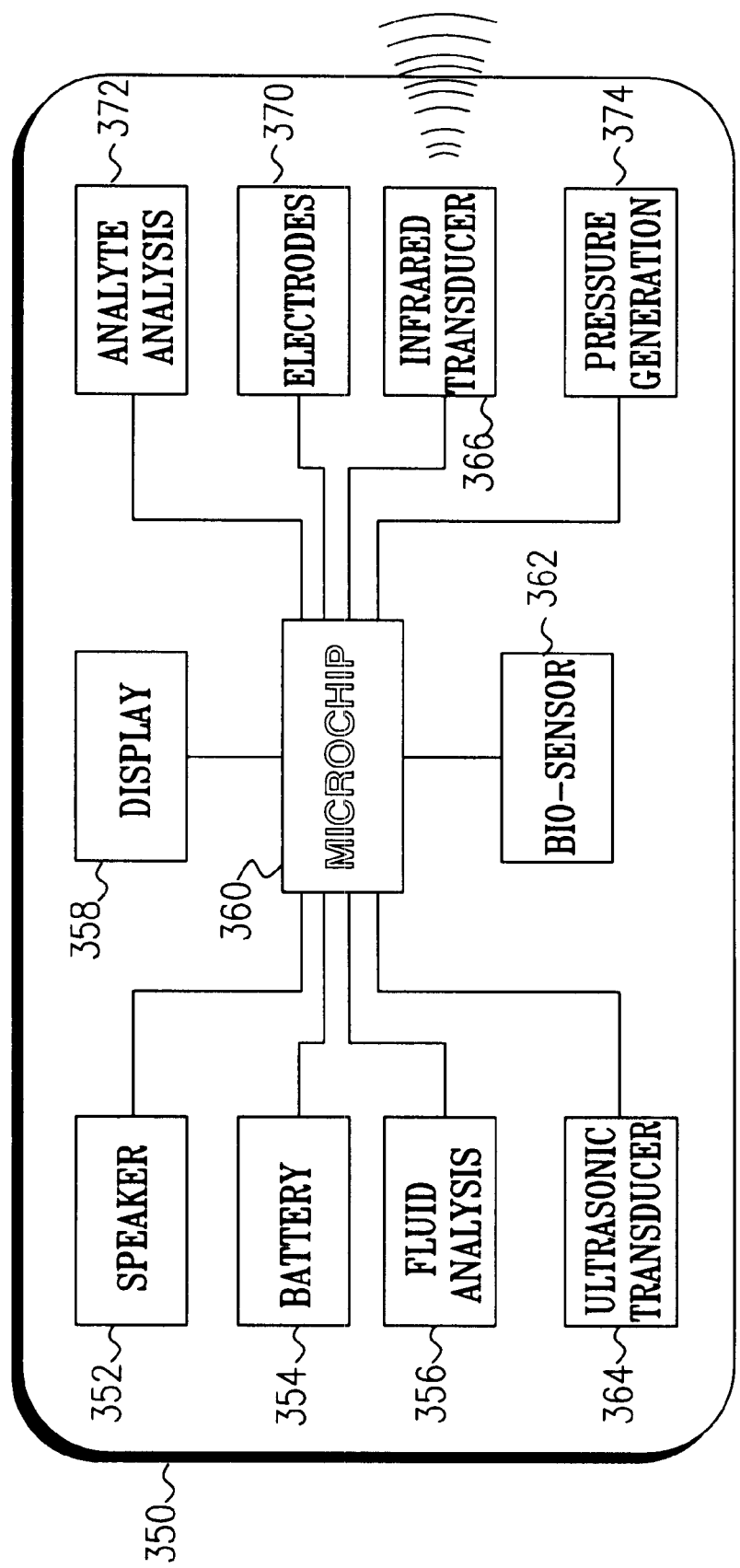
FIG. 13 is a schematic illustration of an electronic card for transdermal drug delivery and analysis of substances, in accordance with a preferred embodiment of the present invention.

FIG. 13 is a block diagram of a device 350, which enables transdermal delivery of an active substance and transdermal analyte extraction, in accordance with a preferred embodiment of the present invention. Preferably, device 350 comprises a plurality of electrodes 370 (arranged, for example, as shown in FIG. 12A), an analyte analysis unit 372, a battery 354, and a microchip controller 360, which controls or receives input from the various components of device

350. Typically, but not necessarily, device 350 is incorporated in a physical package substantially similar to that described hereinabove with respect to electronic drug delivery card 300.

For some applications, device 350 facilitates passage of the active substance through a first ablated area of the skin of the subject, and extracts an analyte through a second ablated area of the skin, in order to determine the level of a relevant biological substance in the subject's blood. For example, the level of the active substance at various time points after the administration thereof may be determined. Alternatively, the device first extracts an analyte through the subject's skin, then analyzes the analyte, and determines responsive thereto the dose or schedule for delivery of the active substance to the subject. For example, an administration schedule of 2 hours on, 2 hours off, may be changed to 3 hours on, 1 hour off, responsive to the analyte analysis. Alternatively or additionally, extraction and analysis of an analyte are performed to determine which of a plurality of active substances stored in device 350 or elsewhere should be delivered to the subject. Analyte extraction following ablation of the skin may be passive, or may be enhanced using various techniques known in the art, e.g., iontophoresis.

For some applications, device 350 additionally comprises a body fluid analysis unit 356, comprising, as appropriate, apparatus for performing blood analysis, urine analysis, or saliva analysis. Typically, the subject deposits a sample of the appropriate body fluid on a designated test site on device 350, and results of an automated analysis serve as inputs to microchip 360 in determining changes in one or more treatment parameters governing operation of the device. For example, one or more of electrodes 370 may be driven to ablate skin under the patch so as to facilitate administration of some of the active substance stored in device 350, or the current level or duration of current applied to the electrodes may be determined based on the results of the analysis of the body fluid. Alternatively or additionally, the type of drug, or the amount of drug to be delivered to the subject is determined responsive to results of the body fluid analysis.

In a preferred embodiment of the present invention, device 350 comprises a bio-sensor 362, which detects other physiological parameters of the subject, such as transepidermal water loss (TEWL), skin electrical impedance, another skin property, blood pressure, temperature, heart rate, or respiration rate. Preferably, these parameters are analyzed to assist microchip 360 in the determination of the type or quantity of active substance to be delivered to the subject. Further preferably, microchip 360 determines the timing of the delivery of the active substance responsive to the measured physiological parameters. For example, electrocardiographic (ECG) readings may be made intermittently or continuously throughout the day, and responsive to an abnormal reading, ablation of the stratum corneum may be initiated to facilitate delivery of a suitable substance (e.g., nitroglycerine). Similarly, the output of bio-sensor 362 may be used to indicate when further ablation is required to facilitate analyte extraction. For example, TEWL and other skin properties are believed to be affected by ablation of the stratum corneum. Water loss through the ablated area, in particular, is believed to increase subsequent to the ablation, and only to decrease when the skin begins to heal and/or when skin permeability decreases. Thus, changes in TEWL or other skin properties are preferably used to indicate when the rate of analyte extraction or substance administration is decreasing, and, if applicable, to indicate that further ablation may be appropriate.

For some applications, device 350 comprises a pressure generation unit 374, which is used to propel the active substance onto ablated regions of skin. Preferably, unit 374 comprises two electrodes immersed in a liquid, and microchip 360 drives a current between the electrodes so as to generate a gas which facilitates the transfer of active substance into the skin.

Alternatively or additionally, device 350 comprises a transport facilitation unit comprising an ultrasonic transducer 364, which is driven by microchip 360 to increase the transfer of the active substance to the skin, e.g., by imparting high energy to molecules of the active substance and/or by enhancing conductance of the skin to the substance.

Further alternatively or additionally, device 350 comprises a transport facilitation unit comprising electrodes, such as some or all of electrodes 370, which are driven to induce iontophoresis or electroporation to improve the transfer of the active substance into the skin of the subject. It is noted that iontophoresis and electroporation are typically performed in addition to, not in replacement of, ablation of the skin. Preferably, these techniques are performed subsequent to ablation of the skin, so as to enhance penetration of the active substance into ablated portions of the skin.

It is noted that any of the transport facilitation units described herein for enhancing drug delivery to the skin (e.g., ablation, pressure generation, ultrasound, iontophoresis, electroporation, mechanical vibrations) can typically be adapted for enhancing analyte extraction from the skin.

For some applications, microchip 360 applies current to some or all of electrodes 370 such that the active substance is delivered to the skin in accordance with a specified schedule. For example, if doses of a medicine are prescribed to be given three times a day, then microchip 360 may drive current every eight hours through a different subset of electrodes 370, such that the medicine in the vicinity of each respective subset is transported into the skin at the appropriate time. Sophisticated administration procedures may be provided, including varying the time of administration and/or the amount of drug administered, by appropriate selection of the time of ablation and the number of electrodes involved. For example:

Before the patient eats breakfast, microchip 360 drives a first number (e.g., 50) of the electrodes to apply currant to ablate the stratum corneum.

Before the patient eats lunch, microchip 360 drives a second number (e.g., 75) of the electrodes to apply current to ablate the stratum corneum.

Before the patient eats a large dinner, microchip 360 drives a third number (e.g., 100) of the electrodes to apply current to ablate the stratum corneum.

Every fifteen minutes from 10 PM to 6 AM, microchip 360 drives a different set of two electrodes to apply current to ablate the stratum corneum.

For some applications, the dose of active substance stored near a given electrode is configured to be largely exhausted following a single ablation event and the resultant delivery of the substance into the skin. For these applications, microchip 360 is preferably adapted to drive different electrodes at each of the administration times.

Alternatively, multiple doses of the active substance may be stored in an inert gel (or other material) near a given electrode, and the concentration of the active substance in the inert gel may be set such that, following a single ablation event by the given electrode, during the period of increased permeability of the skin, a single dose of the active substance will enter the skin. In some cases, the skin "heals" at some point following the ablation, so that further transdermal drug penetration is substantially inhibited at the healed site until a later ablation at that site is initiated by microchip 360. In this manner, microchip 360 (in the above breakfast/lunch/dinner example) could drive at least some of the same electrodes to ablate stratum corneum at each administration time.

Moreover, if two or more different medicines are stored in separate compartments in device 350, each having its own administration schedule, then microchip 360 preferably drives current through the electrodes in a manner so as to facilitate full compliance with the schedules, typically with essentially no input required from the subject.

For some applications, microchip 360 initiates analyte extraction and analysis on a specified schedule, and the active substance is delivered to the skin based on results of the analysis. For example, blood sugar may be tested every hour, and a measured dose of insulin delivered to the subject responsive to the blood sugar level. If appropriate, the microchip is programmed to initiate analyte extraction and analysis a specified amount of time after the active substance has been delivered to the skin. This typically allows the active substance the time to enter the subject and produce the desired effect before testing occurs (e.g., before a re-evaluation of blood sugar levels).

Device 350 preferably comprises a speaker 352 to communicate relevant information to the subject. For example the subject may be informed regarding the status of the device, the outcome of analyte analysis, and the amount of active substance delivered to the subject. Alternatively or additionally, device 350 comprises a display 358, such as an LCD, to present visual information to the subject. As appropriate, device 350 further comprises buttons or a touch screen, which allow the subject to input commands and required information into device 350.

Figure 14:
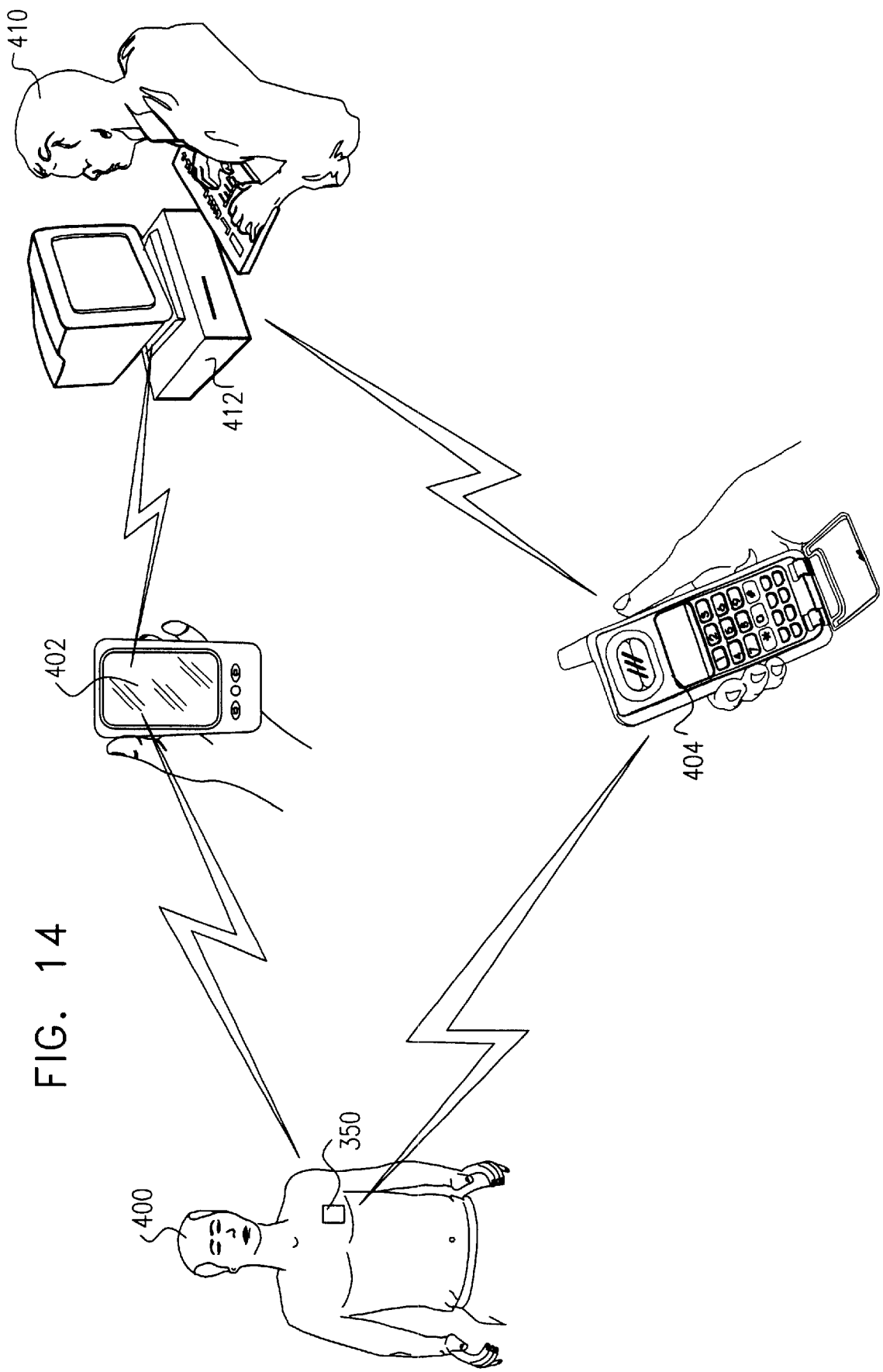
FIG. 14 is a schematic illustration of a system for communicating results from the card in FIG. 13 to a healthcare professional, in accordance with a preferred embodiment of the invention.

Reference is now made to FIGS. 13 and 14. FIG. 14 is a schematic illustration of a system for the communication of health data and treatment instructions for a subject 400, in accordance with a preferred embodiment of the present invention. Typically, the data are sent by device 350 to a computer 412 operated by a health care professional 410, and instructions entered by the health care professional responsive to analyzing the data are sent back to the device. In a preferred application, an infrared transducer 366 (FIG. 13) or other wireless or wired data port transmits to computer 412 information indicative of the amount and timing of drug delivered to the subject, and/or results of analyses performed by device 350. Preferably, the health care professional is enabled to respond to the received information by sending instructions back to device 350, such that the device changes one or more operational parameters thereof responsive to the instructions. For example, results of analyte analysis from device 350 may indicate a need for more frequent treatment by device 350, and health care professional 410 may remotely command device 350 accordingly. Alternatively, the data are analyzed in an automated fashion by computer 412, and instructions are transmitted to device 350 responsive to this automated analysis.

In a preferred embodiment, information from device 350 is transmitted via infrared radiation to a PDA 402, a cellular telephone 404, or another computing or communications device. Alternatively or additionally, information is transmitted from device 350 via radio frequency radiation or by other means known in the art. This information is then preferably downloaded from the PDA or cellular telephone to computer 412 over the Internet or another electronic network.

It is to be understood that the techniques described herein for transdermal delivery of a substance are generally appropriate for many types of substances, including drugs, and broadly including any active agents that include chemical or biological compounds produced either by chemical synthesis or biotechnology routes, including fermentation and/or recombinant technologies.

These drugs may be used or administered to humans or animals or to laboratory animals as an aid in the diagnosis, treatment or prevention of disease or other abnormal conditions, or for the relief of pain or suffering or to control or improve any physiologic or pathologic condition, or for lifestyle improvement, e.g., via cosmetic substances. Drug delivery devices provided by these embodiments of the present invention can be used for administering drugs that are physiologically or pharmacologically active at a point in near relation to the drug delivery device, or for administering a systemically active substance which will produce a physiological or pharmacological response at a site remote from the point of application of the drug delivery device.

The active agents that can be administered by these devices include, therefore, by way of illustration and not limitation;

drugs acting on the immune system, e.g., immunosupressants including Cyclosporine, Sirolimus, Tacrolimus, Mycophenolats Mofetil, central nervous system and anti-dementia drugs including Venlafaxine, Risperidone, Ziprasidone and Flumazenil, L-DOPA; hypnotics, sedatives, and Dopamine agonists, including Bromocriptine, Cabergoline, Pergolide, Pramipexole; Anti-Alzheimer products, including Donepezil, Rivastigmine and Tacrine, Non-Steroidal Anti-Inflammatory and other non-opioid analgesics including Diclofenac (also for topical uses), Acelofenac, Bromfenac, Darbufelone, Dexketoprofen, Diflunisal, Fentoprofen, Floctafenine, Flubiprofen, Ibuprofen, Indomethacin, Ketoprofen, Etodolac, Maclofenamate, Mefenamic acid, Meloxicam, Naproxen, Nabumetone, Phenylbutazone, Piroxicam, Oxprazosin, Sulindac, Tenoxicam, Tiaprofenic acid, Tolmetin, Ketorolac, Narcotic analgesics, including Fentanyl, Anileridine, Buprenophine, Apomorphine, Butarophol, Codeine, Hydrocodone, Hydromorphone, Levorphanol, Meperidime, Methadone, Morphine, Nalbuphine, Opium, Oxycodone, OxyMorphone, Pentazocine, Propoxyphene, Parenteral anesthetics including Atricaine, Lidocaine, Bupivacaine, Chloroprocaine, Etidocaine, Levobupivacaine, Mepivacaine, Prilocaine, Procaine, Tetracaine, Rpivacaine, Cox—2 inhibitors, including Rofecoxib, Celecoxib, and Tramadol, Antimigraine drugs including Sumatriptan, Naratriptan, Zolmitriptan, Rizatriptan, Eletriptan, Almotriptan and Frovatriptan, products designated for neuropathic pain management, including Gabapentin, Pergabalin, drugs useful for alcoholism addiction treatment, including Disulfiram, Naltrexone, LevoMethadyl, post-operative nausea and vomiting products, including Ondansetron, Granisetron, Dolasetron, Nasasetron, Lerisetron, Palonosetron, Tropisetron, Dorabinol, anticoagulants designed for injection, including Heparin, Enoxaparin, Tinzaparin, Antagonists platelet aggregation inhibitors, Eptifibatide, Tirofiban, Dipyridamole, Peripherally-acting corpounds, including Prazosin, Terazosin, Tamsulosin, Doxazosin, BHP treatment drugs, including Finasteride, Bone calcium regulators, e.g., those designated to treat osteoporosis, including Etidronate, Alendronate, Pamidronate, Tiludronate, Clodronate, Ibadronate, Drugs for the treatment of type II diabetes including Rosiglitazoen, Gemcitabine, Glimpride, Miglitol, Acarbose, Rosiglitazone, Products designated to treat attention deficit disorder—MethylPhenydate, Cardiovascular products, including ACE inhibitors and Beta blockers and additional drugs including Tobramycin, Defferoxamine, Argatroban, Mitoxantrone, Anagrelide, Caspofungin, Trisenox, Therapeutic proteins and peptides, including Calcitonin, Desmopressin, Gonadorelin, LHRH, Goserelin, Histerelin, Leuprolide, Lypressin, Nafarelin, Octreotide, Oxytocin, Pentagastrin, Secretin, Vassopressin, Insulin, Sex hormones, e.g., to treat aging symptoms or for use as contraceptives, including Testosterone, Estrogen, Progesterone, Dehydroepiandrosterone, recombinant biopharmaceuticals, including Erythropoietin, Filgrastim, Insulin, Interferon-A, Interferon-B, Energix-B, Interferon Beta, Growth Hormone, Abciximab, Etanercapt, Enbrel, vaccines, nucleotide drugs, including oligonuclectide drugs, polynucleotide drugs hydrophilic compounds, e.g., those which are typically impeded from passing through the stratum corneum, and gene therapy agents, based on DNA, RNA and antisense RNA.

These drugs as well as other substances can be prepared using known techniques, and than used with devices provided by embodiments of the present invention.

It is to be understood that—except where it is explicitly noted otherwise or where it is implicit from context—the methods and apparatus described herein with respect to facilitating substance delivery into the skin may typically be adapted for analyte extraction applications, mutatis mutandis, and, similarly, methods and apparatus described herein with respect to facilitating analyte extraction may be adapted for substance delivery applications, mutatis mutandis.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

What is claimed is:

1. A device for facilitating transdermal passage of a substance through skin of a subject, comprising:
   one or more electrodes, which are adapted to be placed at respective sites on the skin; and
   a control unit, which is adapted:
      to drive at least some of the one or more electrodes to apply to respective ones of the sites on the skin a current capable of ablating stratum corneum epidermidis of the skin, so as to facilitate transdermal passage of the substance through the skin,
      to designate at a first time a first number of the one or more electrodes to drive to apply the current, responsive to a desired rate of passage of the substance during a first time period, and
      to designate at a second time a second number of the one or more electrodes to drive to apply the current, responsive to a desired rate of passage of the substance during a second time period, the second number being different from the first number.

2. A device according to claim 1, wherein the control unit is adapted to drive the current as an alternating current (AC).

3. A device according to claim 2, wherein the control unit is adapted to configure a frequency of the current to be between about 1 kHz and about 300 kHz.

4. A device according to claim 1, wherein the control unit is adapted to drive the current that is capable of causing ablation during a first time period, so as to facilitate passage of the substance through an ablated area of the stratum corneum during a second time period, subsequent to the first time period.

* * * * *